(12) United States Patent
Fisher

(10) Patent No.: US 7,846,428 B2
(45) Date of Patent: Dec. 7, 2010

(54) ARTICULAR CARTILAGE GENE THERAPY WITH RECOMBINANT VECTOR ENCODING BMP-7

(75) Inventor: Laurent Bernard Fisher, Sainte Foy les Lyon (FR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/867,919

(22) Filed: Oct. 5, 2007

(65) Prior Publication Data

US 2009/0093427 A1 Apr. 9, 2009

(51) Int. Cl.
*A61K 48/00* (2006.01)
*C12N 15/86* (2006.01)
*C07H 21/04* (2006.01)
*C12Q 1/68* (2006.01)

(52) U.S. Cl. ............ 424/93.2; 435/456; 536/23.5

(58) Field of Classification Search ............ None
See application file for complete search history.

(56) References Cited

U.S. PATENT DOCUMENTS

| | | | | |
|---|---|---|---|---|
| 5,266,683 | A | * | 11/1993 | Oppermann et al. ........ 530/326 |
| 2003/0220283 | A1 | * | 11/2003 | Glorioso et al. ............. 514/44 |
| 2004/0167088 | A1 | * | 8/2004 | Wickham et al. ............ 514/44 |
| 2004/0223953 | A1 | * | 11/2004 | Kung et al. ................. 424/93.2 |
| 2005/0136042 | A1 | * | 6/2005 | Betz et al. ................... 424/93.21 |
| 2005/0197304 | A1 | * | 9/2005 | DiCesare .................... 514/44 |
| 2007/0190030 | A1 | * | 8/2007 | Pawliuk et al. ............. 424/93.2 |
| 2009/0082301 | A1 | | 3/2009 | Fischer |

FOREIGN PATENT DOCUMENTS

WO WO 2007/056614 5/2007

OTHER PUBLICATIONS

Franceschi, et al. *Gene therapy for bone formation: in vitro and in vivo osteogenic activity of an adenovirus expressing BMP7*. Journal of Cellular Biochemistry. vol. 78, No. 3. (2000) pp. 476-486.
Eto, et al. *Development of PEGylated adenovirus vector with targeting ligand*. International Journal of Pharmaceutics. vol. 354, No. 1-2 (2007) pp. 3-8.
Matthieu, et al. *The conundrum between immunological memory to adenovirus and their use as vectors in clinical gene therapy*. Molecular Biotechnology. vol. 34, No. 2 (2006) pp. 247-256.
Chubinskaya et al. *OP-1/BMP-7 in cartilage repair*. International Orthopaedics. vol. 31, No. 6 (2007) pp. 773-781.
Matthias et al. *Cloning of the 5'-flanking region of the murine bone morphogenetic protein-7 gene*. Molecular and Cellular Biochemistry. vol. 233, No. 1-2 (2002) pp. 31-37.

* cited by examiner

*Primary Examiner*—Quang Nguyen
(74) *Attorney, Agent, or Firm*—Judy Jarecki-Black; Ruoying Chen; Merial Limited

(57) ABSTRACT

The present invention relates to recombinant vectors expressing the BMP-7 polypeptide in host cells and to pharmaceutical compositions comprising such recombinant vectors. The invention also encompasses methods for prevention and/or treatment of osteoarthritis in mammals, advantageously in humans, dogs, horses and cats, by intra-articular administration of the recombinant vectors and pharmaceutical compositions of the invention.

12 Claims, 4 Drawing Sheets

Figure 1

| Animal # | Treatment | Location and Macroscopic Lesions | | | Comments |
|---|---|---|---|---|---|
| | | Medial Femoral Condyle | Tibial Plateau | Patella | |
| 1L | Ad5 BMP-7 | sm. Ptd fsrs | nsf | nsf | Clear improvement L>R |
| 1R | Control | lg ftd, wl, O, mndeg | lat wl | med ftd | |
| 5L | Control | ftd, ptd + fsrs, thin | lg ost, pt fisrs | nsf | Clear improvement R>L |
| 5R | Ad5 BMP-7 | sm area ptd + fsrs, focal repair tissue | sm. Fsrs | nsf | |
| 9L | Ad5 BMP-7 | focal sm thin or fsrs | mild fsrs | | Clear improvement L>R |
| 9R | Control | sm ftd + lg fsrs rt, dp, possible mendeg | pt fsrs thin | nsf | |
| 13L | Control | sm area ftd + fsrs, wr | fsrs | nsf | R has less complete loss of cartilage at injury site than L |
| 13R | Ad5 BMP-7 | sm area ptf with fsrs | fsrs | nsf | |
| 17L | Ad5 BMP-7 | sm area fsrs, limited extension | nsf | nsf | L reduction in size & depth compared to R |
| 17R | Control | larger area fsrs ptd + ftd, expansion clear | nsf | nsf | |
| 20L | Control | ftd and ptd, fsrs moderate radiation from injury | medial thin | fsrs | R clear reduction in size and depth compared to L |
| 20R | Ad5 BMP-7 | focal contained small ptd + limited fsr | nearly normal | nearly normal | |
| 23L | Ad5 BMP-7 | extesnion ftd from injry site, ptd fsrs | nsf | nsf | roughly equivalent though L tibia better than R |
| 23R | Control | extension of ftd from injury site, ptd + fsrs | medial thin | fsrs | |
| 26L | Control | euthanized during experiment due to septicemia and pneumonia | | | |
| 26R | Ad5 BMP-7 | | | | |

| FTD | full thickness defect |
|---|---|
| PTD | Partial thickness defect |
| WL | Wear lines |
| Fsr | Fissures |
| Ost | ostephyte |
| lg | large |
| sm | small |
| med | medial |
| lat | lateral |
| mndeg | meniscal degeneration, fibre separation |
| thin | cartilage thinning |
| nsf | no significant findings |
| rt | repair tissue |
| dp | depressed area | ns, descriptions, product specifications, and product sheets for any products mentioned herein or in any document incorporated by reference herein, are hereby incorporated herein by reference, and may be employed in the practice of the invention.

ARTICULAR CARTILAGE GENE THERAPY WITH RECOMBINANT VECTOR ENCODING BMP-7

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to recombinant vectors, to pharmaceutical compositions comprising such recombinant vectors, and to methods to ensure cartilage repair, and/or slow down osteoarthritis evolution and/or reverse osteoarthritis evolution in vertebrates. The invention also relates to vectors capable of expressing, in a host, a bioactive polypeptide belonging to the Osteogenic Protein-1/Bone Morphogenetic Protein-7 (OP-1/BMP-7) family of proteins. The invention also relates to intra-articular gene therapy with such vectors.

BACKGROUND OF THE INVENTION

Osteoarthritis (OA) is a chronic degenerative disease of the joints of vertebrates. Pain is the predominant presenting symptom of OA. Vertebrates with OA, including humans, mammalian animals, particularly athletic-horses, dogs and cats, have pain that typically worsens with weight bearing and activity and improves with rest, as well as morning stiffness and gelling of the involved joints after periods of inactivity. Such signs and symptoms of the disease often culminate in reductions in quality of life. The disease is more frequent in a subset of the joints of the body, particularly the hips, knees, shoulders, elbows, intercarpus and intertarsus joints.

Diarthrodial joints are organs of locomotion of vertebrates. They achieve almost frictionless motion, thanks to the unique biological, chemical and mechanical properties of the articular cartilage that covers the articulating surfaces of the long bones. Articulation occurs within a synovial cavity, or joint space, whose intimal surface is lined by synovium and within which there normally exits a small volume of lubricating synovial fluid. Certain joints, such as the knee have additional, nonarticular cartilaginous structures, known as menisci. The synovium lines a fibrous capsule, beyond which lies the musculature and ligamentous extra-articular supporting structures of the joint.

Current OA impact in humans is tremendous and rivals that of ischemic heart disease in many regards. As baby boomers reach late adulthood and the obesity epidemic rages on, OA will assume an even greater impact on society. In younger populations, athletes participating in contact sports or activities, such as excessive running, are also at high risk for the development of OA.

In veterinary medicine, OA is very common in horses and dogs but is also recognised in cats, albeit at a lower extend.

In the equine industry, lameness due to joint injury and disease is the most prevalent cause of diminished athletic function and wastage in racing horses. Together, joint injury and joint disease represent a large majority of the equine clinician's caseload. Equine OA can originate from various causes, with trauma and concomitant synovitis being the most common causes of lack of performance in horses. Often OA stems from overuse or conformational inadequacies that predispose an athletic horse to inappropriate biomechanical forces on cartilage.

In the dog, OA is one of the most common chronic musculoskeletal diseases and causes of lameness. It is frequently secondary to congenital or acquired musculoskeletal disorders. Several arthropathies can affect the young dog and lead to secondary OA, including joint dysplasia, osteochondrosis dissecans, un-united anconeal process and patellar luxation. In addition to developmental abnormalities, there are many acquired musculoskeletal disorders associated to cartilage deterioration. In some cases, trauma may directly induce an isolated chondral lesion that can be the onset of an extended and progressive degenerative lesion. After ligamentous lesions, cartilage injuries may appear some weeks later as a consequence of joint instability. Intra-articular fractures are often complicated by secondary cartilage degradation, as a consequence of incomplete fracture reduction. Joint luxation or luxation reduction are commonly complicated by ligament and capsule damage and/or cartilage lesions. Obesity is more and more understood as an important risk factor for OA in dogs as it is in human medicine.

OA is characterized by biochemical and enzymatic changes, cartilage fragmentation and loss, osteophytes formation and bony sclerosis. Although the causes of OA are not completely understood, biochemical stresses affecting the articular cartilage and subchondral bone, biochemical changes in the articular cartilage and synovial membrane, and genetic factors are all important in OA pathogenesis.

Most often, the inflammatory process begins in the synovium, cartilage, joint capsule or subchondral bone and quickly initiates a cascade of inflammatory mediators from the primary tissue of insult. This often causes a "domino effect" of the inflammatory process into the secondary tissues that in turn release inflammatory mediators.

Regardless of the species, the molecular and cellular inflammatory events associated to OA involve the release of metabolites of arachidonic acid in the cell membrane. This in turn initiates pain by means of prostaglandins. Degradation of hyaluronic acid in the joint fluid results from chemoattractants and by-products of the inflammatory pathway, lysosomal enzymes, and non-lysomal enzymes elaborated by injured synoviocytes, and oxygen-derived free radicals from neutrophils and macrophages.

Degeneration of the articular cartilage is considered the sine qua non of OA. Gross findings include fibrillation, erosion and wear lines in the articular cartilage. Histological characteristics include superficial fibrillation, which can progress to form vertical clefts down to subchondral bone. Often the proteoglycan content of the articular cartilage is reduced along with the breakdown of collagen. This results in increased water uptake in cartilage leading to a biomechanically "softer" cartilage surface. These findings can also be accompanied by chondrocyte necrosis and eventual full-thickness loss of articular cartilage. Pathological changes may occur in associated structures as well. Subchondral bone sclerosis commonly accompanies cartilage degeneration, and the demarcation between hyaline and calcified articular cartilage becomes penetrated with blood vessels. Chronic progression of these changes leads to formation of periarticular lipping at the joint margins due to progressive overgrowth of cartilage and subchondral bone along the borders of articulations. The synovial lining and fibrous layer of the joint capsule are altered in OA. The synovium becomes congested, discoloured, and thickened. Histologically, synoviocytes appear hypertrophic, and lymphoplasmacytic cells and macrophages may be present in the subintimal stroma of the synovial tissues.

Numerous medical treatments have been used extensively in the treatment of OA. To date, most treatments have been directed towards lowering and then maintaining a decreased degree of inflammation within damaged joints. Relatively little attention has been focused on therapeutic agents that actually protect the joint tissues and which have been classified by the International League Against Rheumatism (ILAR) guidelines as "disease modifying" OA drugs (DMOADs). Therapy with this class of drugs should, in theory, prevent, retard or reverse morphologic cartilaginous lesions of OA.

Non steroidal anti-inflammatory drugs (NSAIDs) and corticosteroids have been the primary mode of anti-inflammatory therapy. Although non steroidal anti-inflammatory drugs often provide symptomatic relief, little protection and regeneration is afforded to the articular cartilage, nor do the drugs modify the underlying disease process. Many NSAIDs are also associated to significant incidence of undesirable side effects, making their long-term use problematic. Corticosteroids also are commonly used to treat OA and are powerful mediators of reducing pain and inflammation. However, untoward effects on articular cartilage, including impaired chondrocyte activity, decreased glycosaminoglycans and proteoglycans content and decreased cartilage elasticity are reported.

In veterinary practice, aforementioned therapies are sometimes combined for an additive, if not a synergistic, response to joint injury. Often NSAIDs or steroids are combined with hyaluronic acid treatments to improve the viscoelasticity of the joint fluid and boundary lubrication of the intra-articular soft tissues. Patients are also frequently placed on parenteral as well as oral polysulphated glycosaminoglycans (PSGAGs) to sustain or promote chondrocyte metabolic activity and inhibit the detrimental effects of cytokines or prostaglandins on cartilage. While no well-controlled clinical studies have evaluated this "shotgun" approach, each drug has beneficial effects and no adverse effects have been reported to date from using these many different modes of therapy.

Therapeutic intervention in OA is further hindered, in part, by the inability to target therapeutic agents directly into the joints. Traditional oral, intravenous and intramuscular routes are relatively ineffective, because small molecules enter the joint space by passive diffusion and large molecules (such as proteins) are excluded from the joint space. Although intra-articular administration bypasses these limitations, the half-life of most agents directly administered into the joint space remains short and frequent intra-articular injections are needed to sustain biologic activities for prolonged treatments of chronic diseases.

In conclusion, as to date, no therapeutic agent has effectively, and without side effects, eliminated the progression of OA. There is therefore a crying medical need for truly innovative DMOADs strategies for both human and veterinary applications.

Recently, Osteogenic Protein 1 (OP-1), alias Bone Morphogenetic Protein 7 (BMP-7), previously known to promote bone formation and healing, has been demonstrated to play a significant role in articular cartilage regeneration and repair, potentially acting as a DMOADs. Various studies have shown that, when exposed to BMP-7, mesenchymal cells have the potential to differentiate into cells that behave phenotypically as chondrocytes. These cells, both in vitro and in vivo, produce matrix with type II collagen and proteoglycans specific for articular cartilage. This finding has been confirmed in various animal models including a canine large full-thickness osteochondral defect model. The repair tissue obtained has been observed to have hyaline-like appearance and to be maintained over long-term animal studies.

However, the use of BMP-7 for OA therapy is not without limitations and potential complications. Recombinant purified BMP-7 protein in solution is not providing the expected therapeutical benefit when merely injected into a joint because of rapid elimination from the joint space through the synovial vascularisation. Short half-life of the protein within the articulation requires the recombinant BMP-7 protein to be included into an appropriate biological carrier material to ensure slow release and sustained local concentration. The biological carrier further secures the implant stability and physical network for cellular and vascular colonisation leading to cartilage formation. The high concentrations of recombinant protein to be included in the biological carrier (e.g., 340 µg of OP-1 implant administered twice by intra-articular injection one week apart in a sheep post traumatic experimental OA model (Hurtig M B et al., Proceedings Combined Orthopaedic Research Society, 070, October 2004), 350 µg of BMP-7 in bovine-derived type-I collagen device to repair an articular cartilage defect in a canidae surgically induced full thickness osteochondral defect (Cook S. D. et al., J. Bone Joint Surgery, 2003, 85(3): 116-123)). In practical terms, the cost and the complexity of complexing large amounts of purified protein with an appropriate biological carrier makes the procedure non economically viable in veterinary medicine. Further, from a safety standpoint, the use of large quantities of a powerful osteoinductive protein raises the possibility of ectopic bone formation, particularly if the site of implantation is not well contained.

Gene transfer is an attractive strategy to circumvent limitations facing purified recombinant proteins. As gene can be delivered and expressed locally within joints, highest concentrations of therapeutic proteins can be produced in situ within the joint, thereby reducing the likelihood of unwanted side effects to a minimal as non-target organs will receive less exposure. The synovium is an attractive target tissue for gene expression because of its large surface and its direct contact with the joint space. Although the articular cartilage is another available target tissue within the joint, lack of vector penetration through the extracellular matrix is considered an important technical limitation.

Two methods of transferring genes to joints can be considered: ex vivo and in vivo gene transfers.

Ex vivo gene transfer refers to the harvest of cells, their in vitro genetic modification and their subsequent back grafting into the joint. Indeed, accelerated cartilage repair has been demonstrated following transplantation of chondrocytes transduced ex vivo with an Ad5 expressing BMP-7 in an equine cartilage defect model. As this technology allows genetic manipulations outside of the body it is associated to an increased safety profile. However, the approach is facing multiple practical issues as it is time and resources consuming for harvesting, manipulating and re-implanting cells. Further, the longevity of the recombinant protein expression in the chondrocytes transplants remains a limiting factor and requires either very high initial doses or repeat treatments. Clinical applicability of such a strategy is complex and cumbersome, dramatically limiting commercialization potential in veterinary medicine.

In contrast, in vivo gene transfer refers to the direct targeting of synoviocytes or chondrocytes in the joint itself, which is achievable at the clinical level using appropriate vectors. However, this later strategy is also restricted by significant limitations, the exact nature of which depends on the specific vector system that is considered.

Adenoviruses possess many advantages as gene therapy vectors, including the ease to generate high titers of recombinant viruses, the wide range of cell types, including non dividing cells, that are susceptible to efficient transduction by such viruses. The so-called first generation recombinant human adenovirus serotype 5 (Ad5) is based on the deletion of the E1 and potentially the E3 regions of the viral genome. These modifications provide loci for transgene insertion but also result in the prevention of late genes activation, upon which viral replication in target species depends. Such advantages have led to the widespread application of Ad5 vectors both in preclinical and clinical studies. However, the death of a human patient exposed to very large Ad5 doses in 1999 has tarnished the safety record of adenovirus vectors. As of today, the safety of Ad5 vectors administered systemically is considered questionable by many.

However, significant limitations or uncertainties face the utility of this vector for clinical use in joints. The trigger of an anti Ad5 immune response may interfere with the transgene delivery and long-term expression but also may cause pathology, usually inflammatory. Immune and inflammatory interferences have indeed been noticed with recombinant Ad5 delivered intra-articulary in mice, rats, rabbits or horses. Although batch to batch variations and purity may be involved, the amount of viral particles injected intra-articularly appears a key aspect driving Ad5 associated inflammation for intra-articular gene therapy. As the efficacy of the Ad5 vector to trigger expression of the transgene within the joint can be proportional to the injected dose, the selection of the appropriate balance between efficacy and safety for articular gene therapy remains a technical challenge.

The definition of an Ad5 dosage compatible with long-term expression of the recombinant protein within the joint is not clear from existing literature. Indeed, when an Ad5 expressing IGF1 was injected into an equine fetlock joint, significant expression of IGF1 was detectable in the synovial fluid only for those horses receiving very high doses ($50 \times 10^{10}$ viral particles (VP)) (Goodrich L R et al., Gene Therapy, 2006, 13: 1253-1262). No significant expression was noticed with lower doses. This high Ad5 dosage is associated to an increase in white blood cells (WBC) in the synovial fluid, demonstrating a significant local inflammation. Under these conditions, expression of IGF1 peaked at day 4 post injection and declined thereafter. Temporal declines in transgene expression over a period of 2-4 weeks have been observed in other studies using Ad5 as a delivery vector. Although the transient elevation could positively impact cartilage healing in the first 4 weeks and possibly longer, the need for vectors that express proteins for months rather than weeks is considered preferable by many authors in the literature. Indeed, most investigators seeking prolonged gene expression are currently re-orienting their efforts to alternative existing vector systems, such as adeno-associated viruses (AAVs) or lentiviruses.

Prior reports of in vivo usage of recombinant BMP-7 protein for cartilage repair indicated that very high amounts of recombinant protein were required (e.g., 340 µg of OP-1 implant administered twice by intra-articular injection one week apart in a sheep post traumatic experimental OA model (Hurtig M B et al., Proceedings Combined Orthopaedic Research Society, 070, October 2004), 350 µg of BMP-7 in bovine-derived type-I collagen device to repair an articular cartilage defect in a canidae surgically induced full thickness osteochondral defect (Cook S. D. et al., J. Bone Joint Surgery, 2003, 85(3): 116-123)). These amounts are significantly higher than the peak amounts (73 ng/ml) reported in studies using the aforementioned Ad5 IGF1 (Goodrich L R et al., Gene Therapy, 2006, 13: 1253-1262). As a consequence, prior experience with Ad5 vectors for joint gene therapy do not support the use of an Ad5 BMP-7 vector to reach therapeutical concentrations in vivo.

Of further relevance, prior use of high doses of Ad5 BMP7 for in vivo bone formation in immunocompetent rats was unsuccessful whereas the exact same recombinant virus was able to trigger significant bone formation in immunocompromized rats (Li J Z et al., Gene Therapy, 2003, 10: 1735-1743). This example further illustrates the complexity of the prediction of efficacy of an Ad5 BMP7 in vivo.

The technical problem to be addressed is to ensure articular cartilage repair and thereby slow down and potentially reverse osteoarthritis disease evolution in mammals.

Articular cartilage covers the articulating surfaces of the portions of bones in joints. The cartilage allows movement in joints without direct bone-to-bone contact, thereby preventing wearing down and damage of opposing bone surfaces. Articular cartilage has no tendency to ossification. The cartilage surface appears smooth and pearly macroscopically, and is finely granular under high power magnification. Such cartilage is referred to as hyaline cartilage, as opposed to fibrocartilage and elastic cartilage. Articular cartilage appears to derive its nutriment partly from the vessels of the neighboring synovial membrane, partly from those of the bone that it covers. Articular cartilage is associated with the presence of Type II and Type IX collagen and various well-characterized proteoglycans, and with the absence of Type X collagen, which is associated with endochondral bone formation. For a detailed description of articular cartilage micro-structure, see, for example, Aydelotte and Kuettner, Conn. Tiss. Res. 18:205 (1988); Zanetti et al., J. Cell Biol. 101:53 (1985); and Poole et al., J. Anat. 138:13 (1984).

Other types of permanent cartilage in adult mammals include fibrocartilage and elastic cartilage. In fibrocartilage, the mucopolysaccharide network is interlaced with prominent collagen bundles and the chondrocytes are more widely scattered than in hyaline cartilage. Interarticular fibrocartilages are found in those joints which are most exposed to violent concussion and subject to frequent movement, e.g., the meniscus of the knee. Examples of such joints include the temporo-mandibular, sterno-clavicular, acromio-clavicular joints. Elastic cartilage contains collagen fibers that are histologically similar to elastin fibers. Such cartilage is found in the human body in the auricle of the external ear, the Eustachian tubes, the cornicula laryngis, and the epiglottis.

Bone Morphogenetic Protein-7 (BMP-7, or Osteogenic Protein-1, OP-1) is a member of the Transforming Growth Factor-β (TGF-β) superfamily. BMP-7 binds to activin receptors types I and II, but not to TGF-β receptors type I, II and III. Monomeric BMP-7 has a molecular weight of 17 to 19 kDa and was identified by its ability to induce ectopic bone formation. BMP-7 polypeptide is secreted as a homodimer with an apparent molecular weight of approximately 35-36 kDa.

However, because BMP-7 has a short half live in vivo (approximately 30 min), maintenance of a sustained level of exogenous protein in the circulation following injection of the purified protein requires multiple short-interval administrations, creating a very significant practical challenge. The cost of such a multi-injection therapy is too high to be applicable in veterinary medicine. Although gene delivery has been successfully promoted as an alternative to protein therapy for various diseases treatment, it's applicability for osteoarthritis prevention and/or treatment through BMP-7 polypeptide expression in vivo has not been proposed previously, and its potential effectiveness remains uncertain. Indeed, the low molecular weight of the BMP-7 homodimer (i.e., approximately 35 kDa) would theoretically allow for rapid glomerular filtration. Whether or not levels of BMP-7 expressed in vivo could reach therapeutically effective plasma concentrations cannot be predicted or determined from the existing literature. To further complicate the evaluation of in vivo-expressed BMP proteins, results can be variable depending on the immune status of the treated animal, with significant differences between immune competent and incompetent animals. Thus, when considered collectively as a whole, the literature does not teach whether levels of BMP-7 expressed in vivo could reach plasma concentrations that would be therapeutically useful.

Citation or identification of any document in this application does not constitute an admission that such document is available as prior art to the present invention.

SUMMARY OF THE INVENTION

The present invention is directed to methods of prevention and treatment of mammalian subjects who are suffering from, or who are at risk of, osteoarthritis (OA), and to recombinant vectors and pharmaceutical compositions for use in such methods. The methods, vectors and compositions of the invention may be useful for reducing, preventing, inhibiting, delaying, or alleviating the progressive loss of articular function which characterizes osteoarthritis. Subjects for which the methods, recombinant vectors, and compositions of the present invention are useful include, but are not limited to, subjects already afflicted with OA, as well as any subject reasonably expected to suffer from a progressive loss of articular function associated with OA. Whether a particular subject is at risk of OA and/or whether a subject may benefit from the methods and/or compositions of the present invention, is a determination that can be routinely made by one of ordinary skill in the relevant medical or veterinary art. Subjects at risk of OA are notably athletic mammals, like athletes participating in contact sports or activities, such as excessive running, racing horses, racing dogs, dogs of the army and/or police forces, obese mammals (i.e. humans and pets, such as dogs and cats), mammals having congenital or acquired musculoskeletal disorders, old mammals.

In one embodiment the present invention relates to a vector which may contain and express a pre-pro BMP-7 gene, a proBMP-7 gene or a mature BMP-7 gene in a host. The BMP-7 gene encoding the pre-proBMP-7 polypeptide, the proBMP-7 polypeptide or the mature BMP-7 polypeptide may originate from a mammal. In a preferred embodiment, the expression vector may comprise a polynucleotide that encodes a canine pre-proBMP-7, a canine pro-BMP-7 or a canine mature BMP-7 polypeptide. In another preferred embodiment, the expression vector may comprise a polynucleotide that encodes a feline pre-proBMP-7, a feline pro-BMP-7 or a feline mature BMP-7 polypeptide. In another preferred embodiment, the expression vector may comprise a polynucleotide that encodes an equine pre-proBMP-7, an equine pro-BMP-7 or an equine BMP-7 polypeptide. In another preferred embodiment, the expression vector may comprise a polynucleotide that encodes a human pre-proBMP-7, a human pro-BMP-7 or a human mature BMP-7 polypeptide. The polynucleotide encoding the BMP-7 polypeptide may be operatively linked to a promoter and optionally to an enhancer.

In an advantageous embodiment, the invention relates to a vector containing and expressing the canine proBMP-7 polypeptide, wherein the canine proBMP-7 polypeptide is deleted of the "pre" peptide at the N-terminus, and wherein a peptide signal sequence from a different origin is fused to the canine proBMP-7 polypeptide. In another advantageous embodiment, the invention relates to a vector containing and expressing the feline proBMP-7 polypeptide, wherein the feline proBMP-7 polypeptide is deleted of the "pre" peptide at the N-terminus, and wherein a peptide signal sequence from a different origin is fused to the feline proBMP-7 polypeptide. In another advantageous embodiment, the invention relates to a vector containing and expressing the equine proBMP-7 polypeptide, wherein the equine proBMP-7 polypeptide is deleted of the "pre" peptide at the N-terminus, and wherein a peptide signal sequence from a different origin is fused to the equine proBMP-7 polypeptide. In another advantageous embodiment, the invention relates to a vector containing and expressing the human proBMP-7 polypeptide, wherein the human proBMP-7 polypeptide is deleted of the "pre" peptide at the N-terminus, and wherein a peptide signal sequence from a different origin is fused to the human proBMP-7 polypeptide. Advantageously, the peptide signal sequence may be the insulin-like growth factor 1 (IGF-1) or the tissue plasminogen activator (tPA) peptide signal sequence. In another embodiment, the expression vector may comprise a polynucleotide that encodes a canine mature BMP-7 polypeptide wherein said polypeptide is fused with a peptide signal sequence from BMP-7, IGF-1 or tPA. In another embodiment, the expression vector may comprise a polynucleotide that encodes a feline mature BMP-7 polypeptide wherein said polypeptide is fused with a peptide signal sequence from BMP-7, IGF-1 or tPA. In another embodiment, the expression vector may comprise a polynucleotide that encodes an equine mature BMP-7 polypeptide wherein said polypeptide is fused with a peptide signal sequence from BMP-7, IGF-1 or tPA. In another embodiment, the expression vector may comprise a polynucleotide that encodes a human mature BMP-7 polypeptide wherein said polypeptide is fused with a peptide signal sequence from BMP-7, IGF-1 or tPA.

In another embodiment the invention relates to a pharmaceutical composition comprising a vector expressing a pre-proBMP-7 polypeptide, a proBMP-7 polypeptide or a mature BMP-7 polypeptide and a pharmaceutically or veterinarily acceptable carrier, excipient or vehicle. In a particular embodiment, the pharmaceutical composition may comprise a substance to improve the efficacy of transfection or transduction of the vector into the host cells.

In yet another embodiment the invention relates to a method for delivering the BMP-7 polypeptide to a mammal which may comprise injecting intra-articularly into the synovial fluid a vector capable of expressing, in vivo, a pre-proBMP-7 polypeptide, a proBMP-7 polypeptide or a mature BMP-7 polypeptide. In an advantageous embodiment, the mammalian host may be a human, a canidae, an equidae or a felidae, notably man, woman, child, dog, bitch, puppy, horse, mare, foal or cat, kitten. The invention relates to the use of such a vector to prevent and/or treat a mammal for OA.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are described in, or are obvious from and encompassed by, the following Detailed Description.

BRIEF DESCRIPTION OF THE DRAWINGS

The following detailed description, given by way of example but not intended to limit the invention solely to the specific embodiments described, may best be understood in conjunction with the accompanying drawings, in which:

FIG. 1 provides macroscopic data of macroscopic lesions shown on treated and non-treated knees of sheep at necropsy, 90 days after osteoarthritis artificially created by impact.

Figure 2:
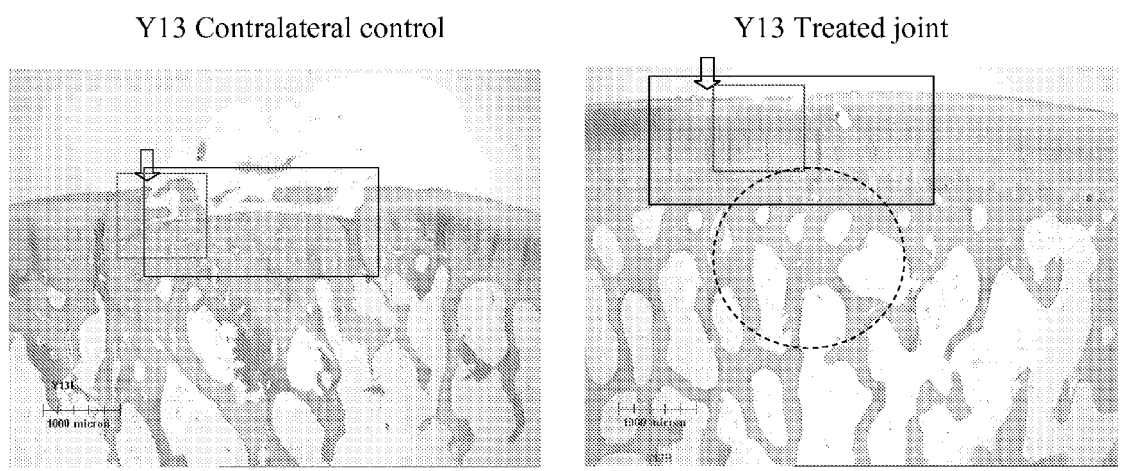
FIG. 2 provide histologic pictures of the left and right knee of one of the animals of Group 1 of the Example 8 (Y13).

Also included as part of the present application is a sequence listing in which: SEQ ID NO: 1 is the nucleotide sequence of the canine pre-proBMP-7 polypeptide, SEQ ID NO: 2 is the codon-optimized nucleotide sequence of the canine pre-proBMP-7 polypeptide, SEQ ID NO: 3 is the amino acid sequence of the canine pre-proBMP-7 polypeptide, SEQ ID NO: 4 is the nucleotide sequence of the short signal peptide from tPA (23 amino acids), SEQ ID NO: 5 is the amino acid sequence of the short signal peptide from tPA (23 amino acids), SEQ ID NO: 6 is the nucleotide sequence of the long signal peptide from tPA (28 amino acids), SEQ ID NO: 7 is the amino acid sequence of the long signal peptide from tPA (28 amino acids), SEQ ID NO: 8 is the nucleotide sequence of the equine IGF-1 signal peptide, SEQ ID NO: 9 is the amino acid sequence of the equine IGF-1 signal peptide, SEQ ID NO: 10 is the nucleotide sequence of the equine pre-proBMP-7 polypeptide, SEQ ID NO: 11 is the nucleotide sequence of the canine IGF-1 signal peptide, SEQ ID NO: 12 is the amino acid sequence of the canine IGF-1 signal peptide, SEQ ID NO: 13 is the nucleotide sequence of the human pre-proBMP-7 polypeptide, SEQ ID NO: 14 is the codon-optimized nucleotide sequence of the human pre-proBMP-7 polypeptide, SEQ ID NO: 15 is the amino acid sequence of the human pre-proBMP-7 polypeptide, SEQ ID NO: 16 is the amino acid sequence of the equine pre-proBMP-7 polypeptide, SEQ ID NO: 17 is the nucleotide sequence of the feline pre-proBMP-7 polypeptide, SEQ ID NO: 18 is the codon-optimized nucleotide sequence of the feline pre-proBMP-7 polypeptide, and SEQ ID NO: 19 is the amino acid sequence of the feline pre-proBMP-7 polypeptide, SEQ ID NO: 20 is the nucleotide sequence of the PB1053 primer, SEQ ID NO: 21 is the nucleotide sequence of the PB1063 primer, SEQ ID NO: 22 is the nucleotide sequence of the PB1060 primer, SEQ ID NO: 23 is the nucleotide sequence of the PB1062 primer, SEQ ID NO: 24 is the nucleotide sequence of the PB1088 primer, SEQ ID NO: 25 is the nucleotide sequence of the PB1089 primer, SEQ ID NO: 26 is the nucleotide sequence of the PB1090 primer, SEQ ID NO: 27 is the nucleotide sequence of the murine pre-proBMP-7 polypeptide, SEQ ID NO: 28 is the amino acid sequence of the murine pre-proBMP-7 polypeptide, SEQ ID NO: 29 is the nucleotide sequence of the LF189 primer, SEQ ID NO: 30 is the nucleotide sequence of the LF190 primer, SEQ ID NO: 31 is the nucleotide sequence of the LF191 primer, SEQ ID NO: 32 is the nucleotide sequence of the LF192 primer, SEQ ID NO: 33 is the nucleotide sequence of the DNA linker, SEQ ID NO: 34 is the nucleotide sequence of the LF327 primer, SEQ ID NO: 35 is the nucleotide sequence of the LF324 primer, SEQ ID NO: 36 is the nucleotide sequence of the LF326 primer, SEQ ID NO: 37 is the nucleotide sequence of the LF325 primer, SEQ ID NO: 38 is the nucleotide sequence of the LF361 primer, SEQ ID NO: 39 is the nucleotide sequence of the LF334 primer, SEQ ID NO: 40 is the nucleotide sequence of the LF437 primer, SEQ ID NO: 41 is the nucleotide sequence of the LF172 primer, SEQ ID NO: 42 is the nucleotide sequence of the LF159 primer, SEQ ID NO: 43 is the nucleotide sequence of the LF377 primer, SEQ ID NO: 44 is the nucleotide sequence of the LF378 primer, SEQ ID NO: 45 is the nucleotide sequence of the SPH6Etr1 primer, SEQ ID NO: 46 is the nucleotide sequence of the SPH6Etr2 primer, SEQ ID NO: 47 is the nucleotide sequence of the SPH6Etr3 primer, SEQ ID NO: 48 is the nucleotide sequence of the SPH6Etr4 primer, SEQ ID NO: 49 is the nucleotide sequence of the SPH6Etr5 primer, SEQ ID NO: 50 is the nucleotide sequence of the SPH6Etr6 primer, SEQ ID NO: 51 is the nucleotide sequence of the SPH6Etr7 primer, SEQ ID NO: 52 is the nucleotide sequence of the SPH6Etr8 primer, SEQ ID NO: 53 is the nucleotide sequence of the LF394 primer, SEQ ID NO: 54 is the nucleotide sequence of the LF395 primer, SEQ ID NO: 55 is the nucleotide sequence of the LF397 primer, SEQ ID NO: 56 is the nucleotide sequence of the LF398 primer, SEQ ID NO: 57 is the nucleotide sequence of the M13R primer, SEQ ID NO: 58 is the nucleotide sequence of the LF409 primer, SEQ ID NO: 59 is the nucleotide sequence of the equine IL10 polypeptide, SEQ ID NO: 60 is the amino acid sequence of the equine IL10 polypeptide, SEQ ID NO: 61 is the nucleotide sequence of the canine IL10 polypeptide, SEQ ID NO: 62 is the amino acid sequence of the canine IL10 polypeptide, SEQ ID NO: 63 is the nucleotide sequence of the feline IL10 polypeptide, SEQ ID NO: 64 is the amino acid sequence of the feline IL10 polypeptide, SEQ ID NO: 65 is the nucleotide sequence of the human IL10 polypeptide, SEQ ID NO: 66 is the amino acid sequence of the human IL10 polypeptide, SEQ ID NO: 67 is the nucleotide sequence of the viral IL10 polypeptide, and SEQ ID NO: 68 is the amino acid sequence of the viral IL10 polypeptide.

DETAILED DESCRIPTION

The methods and compositions of the present invention can be used for therapeutic treatment of OA. The terms "therapy" or "therapeutic treatment", as they relate to OA, and as they are used herein and in the field of veterinary medicine and human medicine, relate to treating mammals that are already suffering from, or are recovering from OA, or treatments aimed at slowing down and/or reversing morphologic cartilaginous lesion evolution in mammals diagnosed as having, or at being at risk of, OA. Whether a particular mammal suffers of OA, can readily be determined by one with ordinary skill in the relevant veterinary or medical art.

As used herein, a mammal is said to suffer from OA, if the mammal is reasonably expected to suffer a progressive loss of articular function associated with considerable loss of cartilage, the generation of wear particles, thickening of synovium and capsule disturbances in the subchondral bone and the growth of osteophytes at the margins of the joint.

The main result of OA in mammals includes, but is not limited to, lameness.

In humans, diagnosis of OA is primarily based on history and physical examination, but radiographic findings, including asymmetric joint space narrowing (JSN), subchondral sclerosis, osteophyte formation, subluxation, and distribution patterns of osteoarthritic changes are all helpful when diagnosis is uncertain. Structural morphological changes on X-rays are also considered the primary outcome variables for assessing the progression of OA. Several indices are currently used for assessing radiological progression of OA, including individual radiographic features (e.g., marginal osteophytes), composite indices (e.g., Kellgren and Lawrence scoring systems), and quantitative measures (e.g., joint space width (JSW) measurement) (Salaffi F. et al., Aging Clin. Exp. Res., 2003, 15(5): 391-404; Buckland-Wright, Osteoarthritis Cartilage, 1999, 7(4): 430-3). Regulatory agencies acknowledge that compounds may be granted a DMOAD indication, providing they demonstrate that they can slow down osteoarthritis disease progression; progression would be calibrated by a surrogate for structural change, by measuring joint space narrowing (JSN) on plain X-rays with the caveat that this delayed JSN translate into a clinical benefit for the patient. Recently, new Magnetic resonance imaging (MRI) technology has been developed to detect a structural change of the OA joint earlier than conventional X-rays and is now used to measure parameters of cartilage morphology and integrity in OA patients (Abadie E. et al., Osteoarthritis Cartilage, 2004, 12(4): 263-8).

Without serial assessments using diagnostic techniques, OA may go undiagnosed until it is advanced. That is frequently the case in mammalian animals, like canidae, felidae or equidae, for which OA is only identified when advanced symptoms appeared, notably lameness.

The present invention provides therapies for OA that utilize pharmaceutical compositions comprising vectors capable of expressing the BMP-7 polypeptide in vivo and methods and composition for inducing a sustained increase in synovial fluid BMP-7 concentration.

As used herein, a pharmaceutical composition according to the invention is said to have "therapeutic efficacy", or to be "therapeutically effective", if administration of that amount of the composition is sufficient to cause a significant improvement of the clinical signs or measurable markers of the disease in a mammalian subject suffering from OA. As used herein, a pharmaceutical composition according to the invention is said to have "prophylactic efficacy" or to be "effective", if administration of that amount of the composition is sufficient to prevent the development of OA in a subject. The term "therapeutically effective" may also be used herein, in a more general sense, to refer to an amount of a composition that is either sufficient to cause a significant improvement of the clinical signs or measurable markers of disease in a mammalian subject suffering from OA, or that is sufficient to prevent the development of OA in a subject.

Experimental demonstration of the efficacy of the methods and compositions of the present invention (e.g. the methods and compositions useful for gene therapy with BMP-7 or functional equivalents of BMP-7), can be performed with a variety of measurable markers, for example, by demonstrating that humans treated using the methods and compositions of the present invention exhibit a significantly reduced diminution of joint space narrowing (JSN) measurement, as compared to placebo-treated humans, when suffering of OA, or by demonstrating that mammalian animals treated using the methods and compositions of the present invention exhibit a significant reduced lameness, and/or a significantly reduced diminution of cartilage thickness measurement on X-rays, as compared to placebo-treated mammalian animals, when suffering of OA. The measurement of cartilage thickness may also be done by echography on equidae.

In one aspect, the present invention relates to a vector capable of expressing, in vivo in a host, a Bone Morphogenetic Protein-7 (BMP-7) polypeptide, or a variant or a fragment thereof As used herein "BMP-7 polypeptide" may be used to refer to pre-pro, pro or mature BMP-7 polypeptides, wherein the pro and mature BMP-7 polypeptides may be fused to a BMP-7, IGF-1 or tPA signal peptide. The BMP-7 polypeptides of the present invention are preferably of canine, feline, equine or human origin. In one embodiment the vector may contain and express in the host a pre-proBMP-7, a proBMP-7 or a mature BMP-7 nucleotide sequence or gene. The nucleotide sequence or gene encoding the pre-proBMP-7 polypeptide, the proBMP-7 polypeptide or the mature BMP-7 polypeptide may originate from a mammal, for example a human, a cat, a horse or a dog. In a preferred embodiment the BMP-7 nucleotide sequence or gene may originate from a dog. In another preferred embodiment the BMP-7 nucleotide sequence or gene may originate from a cat. In another preferred embodiment the BMP-7 nucleotide sequence or gene may originate from a horse. In another preferred embodiment the BMP-7 nucleotide sequence or gene may originate from a human.

BMP-7 is also known as Osteogenic Protein-1 or "OP-1", and is a member of the transforming growth factor-β or "TGF-β" superfamily. It is a secreted protein that is processed from the pro-protein to yield the carboxy-terminal mature protein. Within the mature protein there is a conserved pattern of seven cysteine residues defining a domain that extends from amino acid 330 to amino acid 430 of SEQ ID NO: 3, SEQ ID NO: 15, SEQ ID NO: 16 and SEQ ID NO: 19. The active form of the protein is a disulfide-bonded homodimer. In its mature, native form, naturally occurring BMP-7 is a glycosylated dimer having an apparent molecular weight of about 30-36 kDa, as determined by SDS-polyacrylamide gel electrophoresis ("SDS-PAGE"). When reduced, the 30-36 kDa protein gives rise to two glycosylated polypeptide subunits having apparent molecular weights of about 16 kDa and 18 kDa. The unglycosylated BMP-7 protein has an apparent molecular weight of about 27 kDa. When reduced, the 27 kDa unglycosylated protein gives rise to two unglycosylated polypeptide chains, having molecular weights of about 14 kDa and 16 kDa.

Typically, the naturally occurring BMP-7 protein is translated as a precursor, having an N-terminal signal peptide sequence, a "pro" domain, and a "mature" protein domain. The signal peptide is 29 residues long and is cleaved off rapidly upon translation at a cleavage site that can be predicted using the method of Von Heijne (1986), Nucleic Acid Research, 14; 4683-4691. The "pro" domain has 264 residues in human, canine, feline, swine and bovine BMP-7, and 263 residues in mouse BMP-7. The N-terminal part of the pro BMP-7 is cleaved to yield the "mature" C-terminal domain of 139 residues, which includes the conserved seven-cysteine C-terminal domain of 102 residues. As referred to herein, the "pro form" of the BMP-7 polypeptide refers to a protein comprising a pair of polypeptides, each comprising a pro domain in either covalent or non-covalent association with the mature domain of the BMP-7 polypeptide. The pro form appears to be the primary form secreted from cultured mammalian cells. The "mature form" of the protein refers to the mature C-terminal domain which is not associated, either covalently or non-covalently, with the pro domain.

As used herein the terms "pre-pro BMP-7", "pro BMP-7", "mature BMP-7" and "BMP-7" refer not only to the specific polypeptides and sequences illustrated in the specification and in the accompanying sequence listing, but also refer to any and all of the known naturally occurring variants, of these proteins including, but not limited to, derivatives, mutants, homologues, orthologs, allelic variants, allelic polymorphs, polymorphic variants, phylogenetic counterparts, and also any and all non-naturally occurring variants of these proteins, including but not limited to derivatives, mutants, fragments, fusion proteins, and the like. As used herein, the term "variant" encompasses all such naturally occurring and non-naturally occurring variants. In particular, the present invention encompasses all such variants that retain the feature of being useful for the therapeutic or prophylactic treatment of OA, and/or that retain BMP-7 activity.

These functionally equivalent variants, derivatives, and fragments, and the like display the ability to retain BMP-7 activity. A functional equivalent, as used herein, refers to any BMP-7 variants, derivatives, fragments, and the like that meet either of the following two criteria (a) they have a significant level of amino acid sequence homology with the protein sequence of BMP-7 as described herein, or is encoded by a nucleotide that has a significant level of nucleotide sequence homology with the protein sequence of BMP-7 as described herein; or (b) they have the ability to provide a statistically different response in the treated group as compared to a placebo treated group in an experimental model of osteoarthritis in mammals, like for example the previously described post traumatic osteoarthritis model (PTOA model) (see Hurtig M B et al., Proceedings Combined Orthopaedic Research Society, 070, October 2004; Bolam C. J. et al., AJVR, 2006, 67(3): 433-447). In a typical PTOA model, animals were experimentally exposed to a standardized 30 MPa impact injuries to both (left and right) medial femoral condyles using a 3 cm minimally invasive arthrotomy at day 0 (D0). At day 7 (D7), half of the animals received a dose of 1 mL of a BMP-7 adenovirus vector (Ad5-BMP-7) according to the present invention ($10^9$ virus particles/mL) into the stifle joint of one bruised knee. The administration was done intra-articularly with a syringe and needle into the femoropatellar joint. Injection was done after synovial fluid (1 mL) was collected for various analysis. The contralateral bruised knee was not treated with Ad5-BMP-7. The second half of animals did not receive any treatment and remained as negative control. Serum and synovial fluid were harvested on D0, D14, D21, D28, D60 and D90. On D90, tissues were also collected for macroscopic examination and histology. The results (i.e., lameness evolution, macroscopic data of the knee at necropsy on D90, histology results) on left and right knees were compared for each animal, and also versus the control animals. The animal models may be for example sheep (see Hurtig M B et al., Proceedings Combined Orthopaedic Research Society, 070, October 2004) or horses (see Bolam C. J. et al., AJVR, 2006, 67(3): 433-447).

By way of illustration of variants, derivatives, and the like that may be encompassed by the present invention include, but are not limited to, BMP-7 variants, derivatives, and the like that are encoded by nucleotide sequences that are not exactly the same as the nucleotide sequences disclosed herein, but wherein the changes in the nucleotide sequences do not change the encoded amino acid sequence, or result in conservative substitutions of amino acid residues, deletion of addition of one or a few amino acids, substitution of amino acid residues by amino acid analogues that do not significantly affect the properties of the encoded polypeptides, and the like. Examples of conservative amino acid substitutions include glycine/alanine substitutions; valine/isoleucine/leucine substitutions; asparagine/glutamine substitutions; aspartic acid/glutamic acid substitutions; serine/threonine/methionine substitutions; lysine/arginine substitutions; and phenylalanine/tyrosine/tryptophan substitutions. Other types of substitutions, variations, additions, deletions and derivatives that result in functional BMP-7 derivatives, as described above, are also encompassed by the present invention, and one of skill in the art would readily know how to make, identify, or select such variants or derivatives, and how to test for BMP-7 activity of those variants or derivatives. One of skill in the art may optimize the expression of the BMP-7 polypeptides of the invention by removing cryptic splice sites, by adapting the codon usage, by introducing a Kozak consensus sequence before the start codon, by changing the codon usage or combination thereof to improve expression.

In another embodiment, the present invention may comprise a functional equivalent of a canine pre-proBMP-7 polypeptide having at least 97.5%, at least 98%, at least 98.5% or at least 99% homology or identity with residues 1 to 431 of SEQ ID NO: 3.

In another embodiment, the present invention may comprise a functional equivalent of a human pre-proBMP-7 polypeptide having at least 98%, at least 98.5% or at least 99% homology or identity with residues 1 to 431 of SEQ ID NO: 15.

In another embodiment, the present invention may comprise a functional equivalent of a feline pre-proBMP-7 polypeptide having at least 98.5% or at least 99% homology or identity with residues 1 to 431 of SEQ ID NO: 19.

In another embodiment, the present invention may comprise a functional equivalent of an equine pre-proBMP-7 polypeptide having at least 97.5%, at least 98%, at least 98.5% or at least 99% homology or identity with residues 1 to 431 of SEQ ID NO: 16.

For the purposes of the present invention, sequence identity or homology may be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87: 2264-2268, modified as in Karlin & Altschul, Proc. Natl. Acad. Sci. USA 1993, 90: 5873-5877.

Another example of a mathematical algorithm used for comparison of sequences is the algorithm of Myers & Miller, CABIOS 1988, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988, 85, 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266, 460-480; Altschul et al., Journal of Molecular Biology 1990, 215, 403-410; Gish & States, Nature Genetics, 1993, 3: 266-272; Karlin & Altschul, 1993, Proc. Natl. Acad. Sci. USA 90, 5873-5877; all of which are incorporated by reference herein).

In general, comparison of amino acid sequences may be accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

In a preferred embodiment, the present invention provides a vector that comprises, as insert, a polynucleotide that encodes a canine pre-proBMP-7 polypeptide, and more preferably that contains a polynucleotide that encodes a polypeptide having the amino acid sequence of SEQ ID NO: 3. Preferably this vector contains nucleotides 1 to 1296 of SEQ ID NO: 1.

In another preferred embodiment, the present invention provides a vector that comprises, as insert, a polynucleotide that encodes a human pre-proBMP-7 polypeptide, and more preferably that contains a polynucleotide that encodes a polypeptide having the amino acid sequence of SEQ ID NO: 15. Preferably this vector contains nucleotides 1 to 1296 of SEQ ID NO: 13.

In another preferred embodiment, the present invention provides a vector that comprises, as insert, a polynucleotide that encodes a feline pre-proBMP-7 polypeptide, and more preferably that contains a polynucleotide that encodes a polypeptide having the amino acid sequence of SEQ ID NO: 19. Preferably this vector contains nucleotides 1 to 1296 of SEQ ID NO: 17.

In another preferred embodiment, the present invention provides a vector that comprises, as insert, a polynucleotide that encodes an equine pre-proBMP-7 polypeptide, and more preferably that contains a polynucleotide that encodes a polypeptide having the amino acid sequence of SEQ ID NO: 16. Preferably this vector contains nucleotides 1 to 1296 of SEQ ID NO: 10.

In one embodiment, the peptide signal (prepeptide) sequence spans from the Met residue at position (1) to the Ala residue at position (29), with the numbering of the amino acid residues being that of the pre-proBMP-7 sequence identified as SEQ ID NO: 3, 15, 16 or 19. Cleavage of the signal peptide may occur after the Ala(29) residue. After cleavage of the preBMP-7 peptide, the proBMP-7 polypeptide is secondarily cleaved after the sequence Arg-X-X-Arg(292) (SEQ ID NO:69) to lead to the mature BMP-7 polypeptide.

The terms "protein", "polypeptide" and "polypeptide fragment" are used interchangeably herein to refer to polymers of amino acid residues of any length.

In certain embodiments, the expression vector may comprise a polynucleotide that encodes a mature BMP-7 polypeptide, wherein the polypeptide is fused to a peptide signal sequence that is, or that comprises or is derived from the BMP-7 signal peptide. In other embodiments, the signal peptide sequence may be, or comprise or be derived from, other signal peptides.

The present invention further relates to vectors containing and expressing a polynucleotide encoding the proBMP-7 polypeptide, wherein the pre-BMP-7 signal peptide is deleted and wherein a peptide signal sequence from a different origin is fused to the proBMP-7 polypeptide. For example, in certain embodiments, the peptide signal sequence may be the insulin-like growth factor 1 (IGF-1) or the tissue plasminogen activator (tPA) peptide signal sequence. In a preferred embodiment the proBMP-7 encoded by the polynucleotide is a canine proBMP-7 polypeptide. Advantageously the proBMP-7 is encoded by a polynucleotide nucleotide that is, or comprises, or is derived from nucleotides 88 to 1296 of SEQ ID NO: 1, and that encodes, or comprises an amino acid sequence corresponding to amino acid residues 30 to 431 of SEQ ID NO: 3. In another preferred embodiment, the codon-optimized canine nucleotide sequence corresponding to SEQ ID NO: 2 is used.

In another preferred embodiment the proBMP-7 encoded by the polynucleotide is a human proBMP-7 polypeptide. Advantageously the proBMP-7 is encoded by a polynucleotide nucleotide that is, or comprises, or is derived from nucleotides 88 to 1296 of SEQ ID NO: 13, and that encodes, or comprises an amino acid sequence corresponding to amino acid residues 30 to 431 of SEQ ID NO: 15. In another preferred embodiment, the codon-optimized human nucleotide sequence corresponding to SEQ ID NO: 14 is used.

In another preferred embodiment the proBMP-7 encoded by the polynucleotide is a feline proBMP-7 polypeptide. Advantageously the proBMP-7 is encoded by a polynucleotide that is, or comprises, or is derived from nucleotides 88 to 1296 of SEQ ID NO: 17, and that encodes, or comprises an amino acid sequence corresponding to amino acid residues 30 to 431 of SEQ ID NO: 19. In another preferred embodiment, the codon-optimized feline nucleotide sequence corresponding to SEQ ID NO: 18 is used.

In another preferred embodiment the proBMP-7 encoded by the polynucleotide is an equine proBMP-7 polypeptide. Advantageously the proBMP-7 is encoded by a polynucleotide that is, or comprises, or is derived from nucleotides 88 to 1296 of SEQ ID NO: 10, and that encodes, or comprises an amino acid sequence corresponding to amino acid residues 30 to 431 of SEQ ID NO: 16.

Codon preference among different species can be dramatically different. To enhance the expression level of a foreign protein, it is relevant to match the codon frequency of the foreign protein to the one of the host expression system (Kim et al., Gene, 1997, 199(1-2): 293-301). Codon optimization also optimizes the stability of mRNAs and their export process to the cytoplasm. For codon optimization, other factors than codon frequency can be taken into consideration, e.g. DNA motifs and repeats, secondary structure, GC content, repetitive codons, restriction endonuclease sites, functional motifs like splice site or terminator structure. Algorithms have been created to facilitate the design of the optimal nucleotide sequence. Geneart GmbH (Regensburg, Germany) has developed the proprietary GeneOptimizer™ software (WO-A-04/059556 and WO-A-06/013103) that implements multi-parameter optimization in one single operation. Taking into account the most important parameters in parallel, the software generates a total of up to 500,000 optimized variants of the target sequence in an evolutionary approach and selects the one that is best suited. It has been reported that such optimized genes have up to a 100-fold increase in expression yields compared to the original gene sequence (Bradel-Tretheway et al., J. Virol. Methods, 2003, 111(2): 145-56; Disbrow et al., Virology, 2003, 311(1): 105-14). In embodiments where the nucleotide sequences are codon-optimized, the codon-optimization may be done by Geneart GmbH (Regensburg, Germany) using the GeneOptimizer™ software. The codon-optimization changes only the nucleic acid sequence and not the encoded amino acid sequence.

In embodiments where the signal peptide is derived from the IGF-I signal peptides, it is preferred that the peptide signal may be, or may comprise, or may be derived from, the horse IGF-1 peptide signal, and preferably that defined by amino acid residues 1 to 25 of SEQ ID NO: 9, and encoded by nucleotides 1 to 75 of SEQ ID NO: 8. In alternate embodiments, the IGF-1 peptide signal may be, or may comprise, or may be derived from, the canine IGF-1 peptide signal, and preferably is, or comprises, or is derived from, the canine IGF-1 peptide signal defined by amino acid residues 1 to 25 of SEQ ID NO: 12, and that is encoded by nucleotides 1 to 75 of SEQ ID NO: 11.

In other embodiments, the peptide signal may be, or may comprise, or may be derived from, the tPA peptide signal, such as the human tPA signal peptide. In a preferred embodiment, the tPA signal peptide used, is, or comprises or is derived from, amino acid residues 1 to 23 of the human tPA signal peptide sequence of SEQ ID NO: 5, and is encoded by nucleotides 1 to 69 of SEQ ID NO: 4. In an alternative embodiment, a human tPA signal peptide may be, or may comprise, or may be derived from, amino acid residues 1 to 28 of SEQ ID NO: 7 and is encoded by nucleotides 1 to 84 of SEQ ID NO: 6 may be used.

According to an advantageous embodiment of the invention, the expression vector may comprise the polynucleotides encoding the signal peptide of IGF 1 or tPA according to SEQ ID NO: 5, 7, 9 or 12 fused to the pre-proBMP-7 polypeptide deleted of the signal peptide (corresponding to residue 30 to residue 431). According to another embodiment of the invention, the expression vector comprises the polynucleotides encoding the signal peptide of IGF1 or tPA fused to the mature BMP-7 (corresponding to residue 293 to residue 431).

In some embodiments, the present invention encompasses a vector capable of expressing canine pre-proBMP-7, canine proBMP-7, canine mature BMP-7, human pre-proBMP-7, human proBMP-7, human mature BMP-7, equine pre-proBMP-7, equine proBMP-7, equine mature BMP-7, feline pre-proBMP-7, feline proBMP-7, feline mature BMP-7, or a variant or fragment thereof. For the mature BMP-7 or the proBMP-7, it is preferred that the nucleotide sequence encoding the peptide is preceded immediately by a nucleotide sequence in-frame encoding a peptide signal in order to facilitate the secretion of BMP-7 into the extra cellular medium. The signal sequence can be the natural sequence from the pre-proBMP-7 or a peptide signal from a secreted protein e.g. the signal peptide from the tissue plasminogen activator protein (tPA), in particular the human tPA (S. Friezner Degen et al J. Biol. Chem. 1996, 261, 6972-6985; R. Rickles et al J. Biol. Chem. 1988, 263, 1563-1569; D. Berg. et al Biochem. Biophys. Res. Commun. 1991, 179, 1289-1296), or the signal peptide from the Insulin-like growth factor 1 (IGF1), in particular the equine IGF1 (K. Otte et al. Gen. Comp. Endocrinol. 1996, 102(1), 11-15), the canine IGF1 (P. Delafontaine et al. Gene 1993, 130, 305-306), the feline IGF1 (WO-A-03/022886), the bovine IGF1 (S. Lien et al. Mamm. Genome 2000, 11(10), 877-882), the porcine IGF1 (M. Muller et al. Nucleic Acids Res. 1990, 18(2), 364), the chicken IGF1 (Y. Kajimoto et al. Mol. Endocrinol. 1989, 3(12), 1907-1913), the turkey IGF1 (GenBank accession number AF074980). The signal peptide from IGF1 may be natural or optimized, in particular optimized by removing cryptic splice sites and/or by adapting the codon usage.

As used herein the term "polynucleotide" is used to refer to a polymeric form of nucleotides of any length, which contain deoxyribonucleotides or ribonucleotides.

The present invention further encompasses a vector containing and expressing a polynucleotide encoding a BMP-7 polypeptide operably linked to a promoter element and optionally also linked to an enhancer. In an advantageous embodiment, the promoter is the promoter of the cytomegalovirus (CMV) immediate early gene, preferably from human- or murine-derived CMV. In other embodiments, the enhancers and/or promoters may be selected from among those promoters that are known in the art, and that are suitable for expression of BMP-7 in the vectors of the present invention. Many such promoters are known in the art, and suitable promoters can readily be selected by those of skill in the art. For example, there are various cell and/or tissue specific promoters (e.g., muscle, endothelial cell, liver, somatic cell, and stem cell specific promoters), and various viral promoters and enhancers, and BMP-7 promoters, such as those isogenically specific for each animal species. For example, in one embodiment, if the canine BMP-7 is to be expressed in a canine synoviocytes, the enhancers and/or promoters specific to canine synoviocytes may be used in order to optimize expression of canine BMP-7 for the desired application.

Promoters and enhancers that may be employed in the present invention include, but are not limited to the promoters and enhancers of the LTR of Rous sarcoma virus, the TK gene of HSV-1, the early or late promoters of SV40, the adenovirus major late promoter (MLP), phosphoglycerate kinase genes, metallothionein genes, α-1 antitrypsin genes, albumin genes, collagenase genes, elastase I genes, β-actin genes, β-globin genes, γ-globin genes, α-fetoprotein genes, and muscle creatin kinase genes.

In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No. WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene specific to synoviocytes.

Functional sub fragments of these promoters, i.e., portions of these promoters that maintain an adequate promoting activity, are included within the present invention, e.g. truncated CMV-IE promoters according to PCT Application No.

WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Preferably, the vectors comprise other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344). As to the polyadenylation signal (polyA) for the viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

The term "vector", as used herein, refers to a recombinant adenovirus that comprises a heterologous polynucleotide to be delivered to a target cell, such as in vivo. The heterologous polynucleotide may comprise a sequence of interest for purposes of therapy, and may optionally be in the form of an expression cassette. The heterologous polynucleotide may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of this invention.

The term "recombinant" as used herein means a polynucleotide semisynthetic, or synthetic origin, which either does not occur in nature or is linked to another polynucleotide in an arrangement not found in nature.

The term "heterologous" as used herein derived from a genetically distinct entity from the rest of the entity to which it is being compared. For example, a polynucleotide may be placed by genetic engineering techniques into a plasmid or vector derived from a different source, and is thus a heterologous polynucleotide. A promoter removed from its native coding sequence and operatively linked to a coding sequence other than the native sequence is accordingly a heterologous promoter.

Elements for the expression of canine BMP-7 or feline BMP-7 or human BMP-7 or equine BMP-7 are advantageously present in an inventive vector. In a minimum manner, this may comprise, may consist essentially of, or may consist of an initiation codon (ATG), a stop codon and a promoter, and optionally also a polyadenylation sequence for certain vectors such as, e.g., viral vectors other than poxviruses. When the polynucleotide encodes a polypeptide fragment, e.g. canine BMP-7, advantageously, in the vector, an ATG may be placed at 5' of the reading frame and a stop codon may be placed at 3'. Other elements for controlling expression may be present, such as enhancer sequences, stabilizing sequences, such as intron and signal sequences permitting the secretion of the protein.

Methods for making and/or administering a vector or recombinants for expression of gene products of genes of the invention in vivo can be any desired method, e.g., a method which is by or analogous to the methods disclosed in, or disclosed in documents cited in: Chroboczek J et al., Virol. 1992, 186: 280-285; Yarosh et al., Vaccine, 1996, 14(13): 1257-64; Lutze-Wallace et al., Biologicals, 1995, 23(4):271-7; Falloux F. et al., Human Gene Therapy, 1998, 9: 1909-1917; Shriver J. et al., Nature, 2002, 415: 331-335; Graham F. et al., Methods in Molecular Biology, Vol. 7: Gene Transfer and Expression Protocols Edited by E. Murray, The Human Press Inc, 1991, p 109-128; Ilan Y. et al., Proc. Natl. Acad. Sci., 1997, 94: 2587-2592; Tripathy S. et al., Proc. Natl. Acad. Sci., 1994, 91: 11557-11561; Tapnell B., Adv. Drug Deliv. Rev., 1993, 12: 185-199; Danthinne X. et al., Gene Therapy, 2000, 7: 1707-1714; Berkner K., Bio Techniques, 1988, 6: 616-629; Berkner K. et al., Nucl. Acid Res., 1983, 11: 6003-6020; Chavier C. et al., J. Virol., 1996, 70: 4805-4810.

According to one embodiment of the invention, the expression vector may be a viral vector, in particular an in vivo expression vector. In an advantageous embodiment, the expression vector may be an adenovirus vector. Advantageously, the adenovirus may be a human adenovirus type 5 (hAd5) vector, an E1-deleted and/or an E3-deleted hAd5. Advantageously, the adenovirus may be a canine adenovirus type 2 (CAV-2) vector, an E3-deleted CAV-2 and/or an inserted CAV-2 in the region located between the E4 region and the right ITR region.

In one embodiment the viral vector may be a human adenovirus, in particular a serotype 5 adenovirus, rendered incompetent for replication by a deletion in the E1 region of the viral genome, in particular from about nucleotide 459 to about nucleotide 3510 by reference to the sequence of the hAd5 disclosed in Genbank under the accession number M73260 and in the referenced publication J. Chroboczek et al Virol. 1992, 186, 280-285. The deleted adenovirus can be propagated in either the E1-expressing HEK293 (F. Graham et al J. Gen. Virol. 1977, 36, 59-72) or PER cells, in particular PER.C6 cell lines (F. Falloux et al Human Gene Therapy 1998, 9, 1909-1917). Alternatively, the Ad5 vector can be propagated in any cell line providing transcomplementation for the viral deleted E1 genomic region. The human adenovirus can also be deleted in the E3 region, in particular from about nucleotide 28592 to about nucleotide 30470. Further, the deletion in the E1 region can be done in combination with a deletion in the E3 region (see, e.g. J. Shriver et al. Nature, 2002, 415, 331-335, F. Graham et al Methods in Molecular Biology Vol. 7: Gene Transfer and Expression Protocols Edited by E. Murray, The Human Press Inc, 1991, p 109-128; Y. Ilan et al Proc. Natl. Acad. Sci. 1997, 94, 2587-2592; U.S. Pat. No. 6,133,028; U.S. Pat. No. 6,692,956; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci (region) eventually after a partial or complete deletion of the E1 and/or E3 regions. Advantageously, the polynucleotide to be expressed is inserted under the control of a promoter functional in eukaryotic cells, such as a strong promoter, preferably a cytomegalovirus immediate-early gene promoter (CMV-IE promoter), in particular the enhancer/promoter region from about nucleotide −734 to about nucleotide +7 in M. Boshart et al Cell 1985, 41, 521-530 or the enhancer/promoter region from the pCI vector from PROMEGA Corp. The CMV-IE promoter is advantageously of murine or human origin. The promoter of the elongation factor 1α can also be used. Strong promoters are also discussed herein in relation to plasmid vectors. In one embodiment, a splicing sequence can be located downstream of the enhancer/promoter region. For example, the intron 1 isolated from the CMV-IE gene (R. Stenberg et al J. Virol. 1984, 49, 190), the intron isolated from the rabbit or human β-globin gene, in particular the intron 2 from the β-globin gene, the intron isolated from the immunoglobulin gene, a splicing sequence from the SV40 early gene or the chimeric intron sequence isolated from the pCI vector from Promega Corp. comprising the human β-globin donor sequence fused to the mouse immunoglobulin acceptor sequence (from about nucleotide 890 to about nucleotide 1022 in Genbank under the accession number CVU47120). A poly(A) sequence and terminator sequence can be inserted downstream the polynucleotide to be expressed, e.g. a bovine growth hormone gene, in particular from about nucleotide 2339 to about nucleotide 2550 in Genbank under the accession number BOVBMP-7, a rabbit β-globin gene or a SV40 late gene polyadenylation signal.

In another embodiment the viral vector may be a canine adenovirus (CAV), in particular a CAV-2 (see, e.g. L. Fischer et al. Vaccine, 2002, 20, 3485-3497; U.S. Pat. No. 5,529,780; U.S. Pat. No. 5,688,920; PCT Publication No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment, the vector may be CAV-2 and the insert may be the nucleic acid sequence encoding the canine pre-proBMP-7, the canine proBMP-7 or the canine mature BMP-7 polypeptide, under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

Each human adenovirus vector may comprise or may contain or may consist essentially of, in addition to the polynucleotide encoding the pre-proBMP-7, the proBMP-7 or the mature BMP-7 polypeptide, the BMP-7 polypeptide being preferably from canine origin, equine origin, feline origin, human origin, variant, analog or fragment, operably linked to a promoter or under the control of a promoter or dependent upon a promoter.

The present invention also relates to a pharmaceutical composition comprising a vector expressing in vivo under appropriate or suitable conditions or in a suitable host cell. The pharmaceutical compositions may comprise, may consist essentially of, or may consist of one or more vectors, e.g., expression vectors, such as in vivo expression vectors, comprising, consisting essentially or consisting of and expressing one or more polynucleotides encoding a BMP-7 polypeptide, optionally fused with a BMP-7, IGF-1 or tPA signal peptide, in a pharmaceutically or veterinarily acceptable carrier, excipient or vehicle. Advantageously, the vector may be a human adenovirus and may comprise, may consist essentially of, or may consist of and expresses at least one polynucleotide encoding a canine BMP-7 polypeptide or an equine BMP-7 polypeptide or a feline BMP-7 polypeptide or a human BMP-7 polypeptide, optionally fused with a BMP-7, IGF-1 or tPA signal peptide, in a pharmaceutically or veterinarily acceptable carrier, excipient or vehicle. Thus, according to an embodiment of the invention, the other vector or vectors in the composition may comprise a polynucleotide that encodes, and under appropriate circumstances expresses one or more other proteins, polypeptides or peptides than the canine BMP-7 polypeptide or an equine BMP-7 polypeptide or a feline BMP-7 polypeptide or a human BMP-7 polypeptide.

Compositions containing one or more vectors, may comprise, may consist essentially of, or may consist of polynucleotides encoding, and advantageously expressing, in vivo, a canine BMP-7 polypeptide or an equine BMP-7 polypeptide or a feline BMP-7 polypeptide or a human BMP-7 polypeptide or fusion protein thereof.

In an advantageous embodiment, the invention may provide for the administration of a therapeutically effective amount of a formulation for the delivery and expression of a BMP-7 polypeptide in a target cell. In one embodiment, the formulation comprises an expression vector comprising a polynucleotide that expresses BMP-7 polypeptide and a pharmaceutically or veterinarily acceptable carrier, vehicle or excipient. In an advantageous embodiment, the pharmaceutically or veterinarily acceptable carrier, vehicle or excipient may facilitate transfection and/or may improve preservation of the vector.

For example, a pharmaceutically or veterinarily acceptable carrier or vehicle or excipient can be water or a 0.9% NaCl (e.g., saline) solution or a phosphate buffer. Other pharmaceutically or veterinarily acceptable carrier or vehicle or excipients that can be used for methods of this invention include, but are not limited to, poly(L-glutamate) or polyvinylpyrrolidone. For Ad5 vector, a pharmaceutically or veterinarily acceptable carrier or vehicle or excipient is Tris HCl 10 mM, $MgCl_2$ 1 mM, NaCl 150 mM, Tween-80 54 mg/L, Saccharose 1 M, pH 8.5. The pharmaceutically or veterinarily acceptable carrier or vehicle or excipients may be any compound or combination of compounds facilitating the administration of the vector, increasing the level of expression or increasing the duration of expression. Doses and dose volumes are herein discussed in the general description and can also be determined by the skilled artisan from this disclosure read in conjunction with the knowledge in the art, without any undue experimentation.

Ad5 virus vectors, as other replication-defective recombinant adenovirus vectors, are limited by their propensity to provoke strong innate and adaptive immune responses. Indeed, development of humoral immune responses to the vector by the host leads to neutralizing antibodies and has been shown to preclude efficacy of repeat administrations.

Covalent attachment of polyethylene glycol polymer (PEG) to the surface of the Ad5 virus is a strategy to circumvent neutralizing antibodies by masking the surface of the vector. As PEGylation of Ad5 is compatible with virus infectivity and masks the virus from neutralizing antibodies, PEGylation improves the ability to administer the Ad5 vector on repeated basis.

In a particular embodiment of the invention, the Ad5 virus vector may be PEGylated, that is to say that PEG polymers are covalently attached to the surface of the Ad5 virus.

Such PEGylation may be done by a method comprising the following steps:

(1) Covalent attachment of PEG to the surface of the Ad5 can be achieved using activated PEG tresyl-monomethoxypolyethylene glycol (TMPEG) which reacts preferentially with epsilon-amino terminal of lysine residues of viral hexon, fiber and penton base while preserving a particle to infectious unit ration below 100. TMPEG manufactured according to the procedure of Delgado C. et al., Biotechnol. Appl. Biochem., 1990, 12(2):119-28 can be sourced commercially from Shearwater Polymers (Hultsville, Ala.). The advantage of TMPEG is related to the fact that it can drive coupling under mild physiological conditions, resulting in greater bioactivity.

(2) Prior to PEGylation with TMPEG, virus preparations (in PBS 5% sucrose) are diluted twofold with 130 mM sodium phosphate, pH7, containing 5% sucrose to a final particle concentration of virus of approximatively $1 \times 10^{12}$ particules/ml.

(3) In order to maintain highest infectivity of the virus PEGylation is performed using a PEG-to-virus ratio of 5:1 (mole:mole) using TMPEG at 5% (w/v). PEG coupling reaction is performed on a rotary mixer at room temperature (usually 23-24° C.) during 30 minutes. The reaction is subsequently stopped by lowering the temperature of the reaction to 4° C.

(4) In order to increase the level of PEGylation with TMPEG, the starting TMPEG can be increased to 10% (w/v) during 30 minutes. However this procedure is associated to a reduction in pH that is deleterious to both the virus and the reaction. Since controlling the pH is key, reaction can be performed in 130 mM phosphate, pH7 which provides pH stability over 2 hours and therefore allows PEGylation using 10% TMPEG.

(5) PEGylated vector is subsequently separated from unreacted PEG by CsCl gradient centrifugation or by dialysis against PBS-sucrose (5%).

In a specific embodiment, the pharmaceutical composition may be directly administered in vivo into the joint to be treated, and the encoded product is expressed by the vector in the host articulation. The methods to deliver intra-articularly in vivo a vector encoding a BMP-7 polypeptide, advantageously the canine BMP-7 polypeptide or the equine BMP-7 polypeptide or the feline BMP-7 polypeptide or the human BMP-7 polypeptide, can be modified to deliver the BMP-7 polypeptide, of the present invention to a human, a canidae, an equidae or a felidae notably man, woman, child, dog, bitch, puppy, horse, mare, foal, cat or kitten. The intra-articular in vivo delivery of a vector encoding and expressing the BMP-7 described herein can be accomplished by one of ordinary skill of human or veterinary medicines.

Advantageously, the pharmaceutical compositions and/or formulations according to the invention comprise or consist essentially of or consist of an effective quantity of one or more expression vectors to elicit a therapeutic response as discussed herein; and, an effective quantity can be determined from this disclosure, including the documents incorporated herein, and the knowledge in the art, without undue experimentation.

The therapeutic and/or pharmaceutical composition contains per dose from about $10^7$ to about $10^{11}$, advantageously from about $10^8$ to about $10^{10}$ and more advantageously from about $10^9$ to about $10^{10}$ viral particles (VP) of recombinant human adenovirus expressing BMP-7 polypeptide. The above described dose ranges remain available if the therapeutic and/or pharmaceutical compositions are based on PEGylated human adenovirus vector, notably on PEGylated hAd5 vector. In the case of therapeutic and/or pharmaceutical compositions based on a canine adenovirus vector, notably on CAV-2 vector, a dose can be between about $10^5$ VP and about $10^9$ VP, advantageously between about $10^6$ and about $10^8$, more advantageously between about $10^6$ and about $10^7$ VP of recombinant canine adenovirus expressing canine BMP-7 polypeptide. Titers of adenovirus expressed in virus particles (VP) could be determinate by HPLC and chromatography as describe in paragraph 2.3 of Roitsch C. et al., J Chromatography, 2001, 752: 263-280.

The dose volume of compositions for mammals, e.g., the dose volume of canine compositions, based on adenovirus vectors may be generally between about 0.1 to about 2.0 ml, preferably between about 0.1 to about 1.0 ml, and more preferably between about 0.5 ml to about 1.0 ml.

The present invention may contemplate at least one administration to a mammal of an efficient amount of the therapeutic composition made according to the invention. The mammal may be male, female, pregnant female. In an advantageous embodiment, the mammal may be a human, a canidae or an equidae or a felidae, notably man, woman, child, dog, bitch, puppy, horse, mare, foal, cat, queen or kitten.

The therapeutic composition according to the invention can be administered intra-articularly by a syringe and a needle. The administration may be done by passing through the synovial lining of the articulation to be treated and by injecting the therapeutic composition according to the invention into the synovial fluid.

It should be understood by one of skill in the art that the disclosure herein regarding administration of the compositions of the invention is provided by way of example, and that the present invention is not limited to the specific examples described. From the disclosure herein, and from the knowledge in the art, the skilled artisan can determine the number of administrations, the administration route, and the doses to be used for each administration of the compositions of the present invention without any undue experimentation.

In a preferred embodiment, the present invention relates to the use of, and to compositions comprising, a viral vector encoding and capable of expressing, a canine pre-proBMP-7, a canine proBMP-7, a canine BMP-7 mature polypeptide, human pre-proBMP-7, human proBMP-7, human mature BMP-7, equine pre-proBMP-7, a equine proBMP-7, a equine BMP-7 mature polypeptide, feline pre-proBMP-7, feline proBMP-7, feline mature BMP-7, or a variant, derivative or fragment thereof, for the treatment and/or prevention of OA by intra-articular injection.

The pharmaceutical composition according to the present invention, comprising vectors capable of expressing the BMP-7 polypeptide in vivo, and which provides therapies for OA, can also be administered to mammalian subjects, which are simultaneously treated with at least one active non steroidal anti-inflammatory drugs (NSAID'S) ingredient.

The present invention provides also a method of treating a mammalian subject suffering from osteoarthritis, comprising, administering intra-articularly to said mammalian subject a therapeutically effective amount of a composition comprising at least one pharmaceutically or veterinarily acceptable carrier, excipient, or vehicle, recombinant adenovirus vectors containing a nucleic acid sequence encoding a BMP-7 polypeptide operatively linked to a promoter, wherein the mammalian subject is simultaneously treated with at least one active NSAID'S ingredient and the BMP-7 polypeptide is expressed in vivo in the mammalian subject.

In a particular embodiment, active NSAID'S ingredients are provided to the treated mammalian subjects between about 10 days before and about 10 days after the administration of the pharmaceutical composition comprising vectors capable of expressing the BMP-7 polypeptide in vivo. Preferably, active NSAID'S ingredients are provided between about 5 days before and about 5 days after the administration of the pharmaceutical composition comprising vectors capable of expressing the BMP-7 polypeptide in vivo. Most preferably, active NSAID'S ingredients are provided between about 2 days before and about 2 days after the administration of the pharmaceutical composition comprising vectors capable of expressing the BMP-7 polypeptide in vivo.

The administration of NSAID'S may be done orally, topically, parenterally, by inhalation spray or rectally in dosage unit formulations containing conventional non-toxic pharmaceutically acceptable carriers, adjuvants and vehicles. The term parenteral as used herein includes subcutaneous injection, intravenous, intramuscular, intrasternal injection or infusion techniques.

The pharmaceutical compositions containing the active NSAID'S ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active NSAID'S ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active NSAID'S material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active NSAID'S ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active NSAID'S ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The NSAID'S may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The compositions of NSAID'S may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parentally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acid such as oleic acid fin use in the preparation of injectables.

NSAID'S compound may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the NSAID'S compound are employed. Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active NSAID'S ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the osteoarthritis.

In a particular embodiment, the NSAID'S may be COX-2 (cyclooxygenase-2) inhibitors. The COX-2 inhibitors may be co-administered, as previously described, to the mammalian subject treated by intra-articular injection of a therapeutic composition according to the present invention for the treatment and/or prevention of OA. As with other NSAIDs, COX-2 inhibitors are effective in treating cyclooxygenase mediated diseases such as inflammation, analgesia and fever. These compounds are especially effective in treating cancer, rheumatoid arthritis and osteoarthritis. These compounds have the advantage of not affecting the integrity of the gastrointestinal tract and the renal blood flow. Examples of these compounds include (methylsulfonyl)phenyl-2-5(H)-furanone derivatives. These derivatives are described, for example, in U.S. Pat. No. 5,981,576. Preferably, the COX-2 inhibitors are selected among the compounds of Formula I as described in the granted U.S. Pat. No. 6,169,188. Especially preferred COX-2 inhibitors include 3-(cyclopropylmethoxy)-5,5-dimethyl-4-(4-methylsulfonyl)phenyl)-5H-furan-2-one or 3-(cyclopropylethoxy)-5,5-dimethyl-4-(4-methylsulfonyl)phenyl)-5H-furan-2-one or pharmaceutically acceptable salts or hydrates of these compounds. An especially preferred COX-2 inhibitor is polymorphic form B of 3-(cyclopropylmethoxy)-4-[4(methylsulfonyl)phenyl]-5,5-dimethyl-5H-furan-2-one.

For horses, the doses of COX-2 inhibitors may be from about 0.05 to about 0.5 mg/kg per 12-24 h as an oral or parenteral administration (notably intravenous, subcutaneous or intramuscular administration) and more preferably about 0.1 mg/kg per 24 h. Preferably Cox-2 inhibitors are oral liquid suspension or solution, viscous liquid, gel, paste or intravenous/subcutaneous/intramuscular formulation.

For dogs, the doses of COX-2 inhibitors may be from about 2 to about 10 mg/kg per 12-24 h, preferably from about 5 to about 10 mg/kg per 24 h, and more preferably about 5 mg/kg per 24 h. Preferably Cox-2 inhibitors are an oral tablet (classic hard, chewable or soft chewable), oral liquid suspension or solution, or intravenous/subcutaneous/intramuscular formulation.

Some examples of pastes comprising COX-2 inhibitors are described in the patent application EP-A1-1.688.149, notably in tables 10-12.

The present invention provides further therapies for OA that utilize pharmaceutical compositions comprising vectors capable of expressing in vivo the BMP-7 polypeptide and at least one interleukine-10 (IL10), and thereby providing methods and composition for inducing a sustained increase in synovial fluid BMP-7 concentration and IL10 concentration.

The present invention provides further a method of treating a mammalian subject suffering from osteoarthritis, comprising, administering intra-articularly to said mammalian subject a therapeutically effective amount of a composition comprising at least one pharmaceutically or veterinarily acceptable carrier, excipient, or vehicle, recombinant adenovirus vectors containing a nucleic acid sequence encoding a BMP-7 polypeptide operatively linked to a promoter, and recombinant viral vectors containing a nucleic acid sequence encoding a IL10 polypeptide operatively linked to a promoter, wherein the BMP-7 polypeptide and the IL10 polypeptide are expressed in vivo in the mammalian subject.

In another particular embodiment, the present invention relates to the use of, and to compositions comprising, a viral vector encoding and capable of expressing, a canine pre-proBMP-7, a canine proBMP-7, a canine BMP-7 mature polypeptide, human pre-proBMP-7, human proBMP-7, human mature BMP-7, equine pre-proBMP-7, a equine proBMP-7, a equine BMP-7 mature polypeptide, feline pre-proBMP-7, feline proBMP-7, feline mature BMP-7, or a variant, derivative or fragment thereof, and another viral vector encoding and capable of expressing, interleukine-10 (IL10), notably equine IL10, canine IL10, feline IL10, human IL10, viral IL10 for the treatment and/or prevention of OA by intra-articular injection. In a preferred embodiment, the present invention relates to the use of, and to compositions comprising, a viral vector encoding and capable of expressing, a canine pre-proBMP-7, a canine proBMP-7, a canine BMP-7 mature polypeptide, or a variant, derivative or fragment thereof, and another viral vector encoding and capable of expressing, canine IL10 for the treatment and/or prevention of OA by intra-articular injection. In another preferred embodiment, the present invention relates to the use of, and to compositions comprising, a viral vector encoding and capable of expressing, an equine pre-proBMP-7, an equine proBMP-7, an equine BMP-7 mature polypeptide, or a variant, derivative or fragment thereof, and another viral vector encoding and capable of expressing, equine IL10 for the treatment and/or prevention of OA by intra-articular injection. In another preferred embodiment, the present invention relates to the use of, and to compositions comprising, a viral vector encoding and capable of expressing, a feline pre-proBMP-7, a feline proBMP-7, a feline BMP-7 mature polypeptide, or a variant, derivative or fragment thereof, and another viral vector encoding and capable of expressing, feline IL10 for the treatment and/or prevention of OA by intra-articular injection. In another preferred embodiment, the present invention relates to the use of, and to compositions comprising, a viral vector encoding and capable of expressing, a human pre-proBMP-7, a human proBMP-7, a human BMP-7 mature polypeptide, or a variant, derivative or fragment thereof, and another viral vector encoding and capable of expressing, human IL10 for the treatment and/or prevention of OA by intra-articular injection. Preferably, the "another viral vector" is an adenovirus vector, notably a human adenovirus or a canine adenovirus, in particular hAd5 vector or CAV2 vector. When such combinations of vectors are used, the administration is done as previously described for compositions comprising only adenovirus vectors expressing BMP-7 polypeptide, except that the therapeutic and/or pharmaceutical composition contains per dose from about $10^7$ to about $10^{11}$ VP of adenovirus vectors expressing BMP-7 polypeptide and from about $10^7$ to about $10^{11}$ VP of adenovirus vectors expressing IL10 polypeptide; advantageously from about $10^8$ to about $10^{10}$ VP of adenovirus vectors expressing BMP-7 polypeptide and from about $10^8$ to about $10^{10}$ VP of adenovirus vectors expressing IL 10 polypeptide; and more advantageously from about $10^9$ to about $10^{10}$ VP of adenovirus vectors expressing BMP-7 polypeptide and from about $10^9$ to about $10^{10}$ VP of adenovirus vectors expressing IL10 polypeptide. In the case of therapeutic and/or pharmaceutical compositions based on a canine adenovirus vector, notably on CAV-2 vector, a dose can be between about $10^5$ VP and about $10^9$ VP, advantageously between about $10^6$ and about $10^8$, more advantageously between about $10^6$ and about $10^7$ VP of recombinant canine adenovirus.

The present invention provides further a method of treating a mammalian subject suffering from osteoarthritis, comprising, administering intra-articularly to said mammalian subject a therapeutically effective amount of a composition comprising at least one pharmaceutically or veterinarily acceptable carrier, excipient, or vehicle, recombinant adenovirus vectors containing a nucleic acid sequence encoding a BMP-7 polypeptide operatively linked to a promoter and a nucleic acid sequence encoding a IL10 polypeptide operatively linked to a second promoter, wherein the BMP-7 polypeptide and the IL10 polypeptide are expressed in vivo in the mammalian subject.

In another particular embodiment, the present invention relates to the use of, and to compositions comprising, a viral vector encoding and capable of expressing both, a canine pre-proBMP-7, a canine proBMP-7, a canine BMP-7 mature polypeptide, human pre-proBMP-7, human proBMP-7, human mature BMP-7, equine pre-proBMP-7, a equine proBMP-7, a equine BMP-7 mature polypeptide, feline pre-proBMP-7, feline proBMP-7, feline mature BMP-7, or a variant, derivative or fragment thereof, and encoding and interleukine-10 (IL10), notably equine IL10, canine IL10, feline IL10, human IL10 for the treatment and/or prevention of OA by intra-articular injection. In a preferred embodiment, the present invention relates to the use of, and to compositions comprising, a viral vector encoding and capable of expressing both, a canine pre-proBMP-7, a canine proBMP-7, a canine BMP-7 mature polypeptide, or a variant, derivative or fragment thereof, and canine IL10 for the treatment and/or prevention of OA by intra-articular injection. In another preferred embodiment, the present invention relates to the use of, and to compositions comprising, a viral vector encoding and capable of expressing both, an equine pre-proBMP-7, an equine proBMP-7, an equine BMP-7 mature polypeptide, or a variant, derivative or fragment thereof, and equine IL10 for the treatment and/or prevention of OA by intra-articular injection. In another preferred embodiment, the present invention relates to the use of, and to compositions comprising, a viral vector encoding and capable of expressing both, a feline pre-proBMP-7, a feline proBMP-7, a feline BMP-7 mature polypeptide, or a variant, derivative or fragment thereof, and feline IL10 for the treatment and/or prevention of OA by intra-articular injection. In another preferred embodiment, the present invention relates to the use of, and to compositions comprising, a viral vector encoding and capable of expressing both, a human pre-proBMP-7, a human proBMP-7, a human BMP-7 mature polypeptide, or a variant, derivative or fragment thereof, and human IL10 for the treatment and/or prevention of OA by intra-articular injection. When such two insert vectors are used, the administration is done as previously described for compositions comprising only adenovirus vectors expressing BMP-7 polypeptide.

Nucleic acid sequences encoding IL10 can be found in Internet databases, notably in Genbank database under the accession number U38200 and region [1-537] for equine IL10, XM_850467.1 and region [2-541] for canine IL10, NM_001009209.1 and region [1-537] for feline IL10, NM_000572.2 and region [60-596] for human IL10, and AF182315 for viral IL10.

As defined for BMP-7, functional equivalents of IL10, variants of IL10, derivatives of IL10, and the like are encompassed by the present invention. Functional equivalents of IL10 are defined by the biological activities and properties of IL10, whose activities and properties are notably described in Schlaak J F et al., J Immunol Methods, 1994, 168(1): 49-54.

In a particular embodiment, the present invention may comprise a functional equivalent of an equine IL10 polypeptide having at least 90%, at least 91%, at least 92%, at least 93%, at least 94%, at least 95%, at least 96%, at least 97%, at least 98% or at least 99% homology or identity with SEQ ID NO: 60.

In another particular embodiment, the present invention may comprise a functional equivalent of a canine IL 10 polypeptide having at least 90%, at least 91%, at least 92%, at least 93%, at least 94%, at least 95%, at least 96%, at least 97%, at least 98% or at least 99% homology or identity with SEQ ID NO: 62.

In another particular embodiment, the present invention may comprise a functional equivalent of a feline IL10 polypeptide having at least 90%, at least 91%, at least 92%, at least 93%, at least 94%, at least 95%, at least 96%, at least 97%, at least 98% or at least 99% homology or identity with SEQ ID NO: 64.

In another particular embodiment, the present invention may comprise a functional equivalent of a human IL10 polypeptide having at least 90%, at least 91%, at least 92%, at least 93%, at least 94%, at least 95%, at least 96%, at least 97%, at least 98% or at least 99% homology or identity with SEQ ID NO: 66.

In another particular embodiment, the present invention may comprise a functional equivalent of a viral IL10 polypeptide having at least 90%, at least 91%, at least 92%, at least 93%, at least 94%, at least 95%, at least 96%, at least 97%, at least 98% or at least 99% homology or identity with SEQ ID NO: 68.

The promoters for the expression of IL10 are the same than those described previously for BMP-7 expression.

The invention will now be further described by way of the following non-limiting examples.

EXAMPLES

Example 1

Generation of the Feline BMP-7 Gene

The cDNA of the BMP-7 was obtained by RT-PCR using purified RNA from feline kidney cells. Total RNA was prepared from feline kidney cells obtained from kidney from foal using the RNeasy Mini Kit (Qiagen, Courtaboeuf, France) according to the manufacturer's protocol.

The reverse transcriptase (RT) step was performed using the One Step Superscript III Kit (Invitrogen, New Jersey, USA, Ref: 12574.035) according to the manufacturer's protocol. The cDNA fragment corresponding to the feline BMP-7 gene was then amplified by polymerase chain reaction (PCR) using 2 couples of primers PB1053-PB1063 and PB1060-PB1062 according to the GenBank available sequences (human BMP-7 under the accession number AL122058, murine under the accession number NM_007557 and canine under the accession number XM_862341).

```
PB1053 (SEQ ID NO: 20) (31 mer):
5' GGATCCCTAGTGGCAGCCACAGGCTCGGACG 3'

PB1063 (SEQ ID NO: 21) (24 mer):
5' GCCACCAGCAACCACTGGGTGGTC 3'

PB1060 (SEQ ID NO: 22) (24 mer):
5' TTCAGCCTGGACAACGAGGTGCAC 3'

PB1062 (SEQ ID NO: 23) (20 mer):
5' TGGTTGGTGGCGTTCATGTA 3'
```

The RT-PCR conditions were:

| Cycle | Step1 | Step2 | Step3 |
|---|---|---|---|
| 1 | 52° C. - 30 min | | |
| 2 | 94° C. - 2 min | | |
| 3-48 | 94° C. - 15 sec | Gradient of temperature (50° C.-60° C.) - 30 sec | 68° C. - 1 min 30 |
| 49 | 68° C. - 5 min | | |

The last cycle was performed with the Taq Polymerase (Life Technologies, Cergy Pontoise, France) to allow an extra A to be incorporated at the 5' end of the transcripts.

The PCR fragment (698 base pairs (bp)—amplification with primers PB1053-PB1063) was purified from an agarose gel using UltraClean™ 15 DNA Purification Kit (MoBio Laboratories, Inc., USA) and cloned into the pCR2.1 vector (TA Cloning Kit, Invitrogen, ref: 45-0641) to generate the plasmid pPB759 (4546 bp).

The PCR fragment (1036 bp—amplification with primers PB1060-PB1062) was purified from an agarose gel using UltraClean™ 15 DNA Purification Kit (MoBio Laboratories, Inc., USA) and cloned into the pCR2.1 vector (TA Cloning Kit, Invitrogen, ref: 45-0641) to generate the plasmid pPB761 (4968 bp).

Plasmid pPB759 was digested with BstEII and NotI to obtain a BstEII-NotI fragment (394 bp). Plasmid pPB761 was digested with BstEII and NotI to obtain a BstEII-NotI fragment (4749 bp). The two fragments were ligated to generate plasmid pPB758 (5143 bp).

The identity of pPB758 was confirmed by BamHI and PstI digestions.

Cloning the 5' flanking region of the feline BMP-7 was based on the strong homology of the intron sequence downstream of the BMP-7 gene for the different species.

A semi-nested PCR was performed using the forward primer PB1088 localized in the sequence of the intron and two different reverse primers PB 1089 and PB 1090.

The first PCR was performed with primers PB1088-PB1089 and DNA genomic extract from CRFK cells (Crandell-Ress Feline Kidney cells) as template and the Phusion™ High-Fidelity DNA Polymerase (Finnzymes, ref: F-518).

The PCR conditions were:

| Cycle | Step1 | Step2 | Step3 |
|---|---|---|---|
| 1 | 98° C. - 30 sec | | |
| 2-30 | 98° C. - 10 sec | Gradient of temperature (45° C.-65° C.) - 30 sec | 72° C. - 15 sec |
| 31 | 68° C. - 10 min | | |

The second PCR (nested PCR) was performed with primer PB1088 and primer PB1090 using the 100-fold diluted first PCR reaction as template. The reaction was allowed to proceed under the same conditions as those for the first reaction.

```
PB1088 (SEQ ID NO: 24) (23 mer):
5' GGGTAGCGCGTAGAGCCGGCGCG 3'.

PB1089 (SEQ ID NO: 25) (22 mer):
5' CGTCGGTGAGGAAGCGGCTCTA 3'.

PB1090 (SEQ ID NO: 26) (22 mer):
5' GGATCTCGCGCTGCATCTCCCG 3'.
```

The PCR fragment (190 bp-amplification with primers PB1088-PB1090) was purified from an agarose gel using UltraClean™ 15 DNA Purification Kit (MoBio Laboratories, Inc., USA) and cloned into the pCR2.1 vector (TA Cloning Kit, Invitrogen, ref: 45-0641) to generate the plasmid pPB770 (4129 bp).

The feline BMP-7 open reading frame (ORF) was entirely sequenced and the nucleotide sequence and amino acid sequence were given under the SEQ ID NO: 17 and SEQ ID NO: 19, respectively.

Example 2

Construction of the Ad5 Adenovirus Vector Having Murine BMP-7 Insert

The nucleic acid and amino acid sequences of the murine BMP-7 are available on GenBank database under the accession number NM_007557.

The murine BMP7 ORF consists of a nucleotide sequence of 1293 bp (SEQ ID NO: 27) and encodes a 430 amino acids polypeptide (SEQ ID NO: 28).

To prepare adenovirus vectors, the nucleotide sequence SEQ ID NO: 27 of the murine BMP-7 polypeptide was amplified by PCR using primers that add FseI and AscI restriction sites at the 5' and 3' termini, respectively. PCR primers were used with a template containing the full-length BMP-7 cDNA in a PCR reaction as follows: incubation at 95° C. for 5 minutes; followed by 15 cycles at 95° C. for 1 min., 58° C. for 1. min., and 72° C. for 1.5 min.; followed by 72° C. for 7 min.; followed by a 4° C. soak. The reaction products were loaded onto a 1.2% (low melt) (SeaPlaque GTG™; FMC, Rockland, Me., USA) gel in TAE buffer. The BMP-7 PCR product was excised from the gel and purified using a spin column containing a silica gel membrane (QIAquick™ Gel Extraction Kit; Qiagen, Inc., Valencia, Calif., USA) as per kit instructions. The BMP-7 product was then digested with FseI and AscI enzymes. The cDNA was isolated on a 1% low melt agarose gel, and was then excised from the gel. The gel slice was melted at 70° C., extracted twice with an equal volume of Tris-buffered phenol, and EtOH precipitated. The DNA was resuspended in 10 μl $H_2O$.

The BMP-7 cDNA was cloned into the FseI-AscI sites of a pAdTrack CMV plasmid (He et al., Proc. Natl. Acad. Sci. USA, 1998, 95: 2509-2514). This construct contained further a green fluorescent protein (GFP) marker gene, a CMV promoter and a SV40 polyadenylation signal. In order to linearize the plasmid, approximately 5 μg of the plasmid was digested with PmeI enzyme. Approximately 1 μg of the linearized plasmid was cotransformed with 200 ng of supercoiled pAdEasy (He et al., supra) into BJ5183 bacterial cells. The co-transformation was done using a Bio-Rad Gene Pulser at 2.5 kV, 200 ohms and 25 μF. The entire co-transformation was plated on 4 LB plates containing 25 μg/ml kanamycin. The smallest colonies were picked and expanded in LB/kanamycin, and recombinant adenovirus DNA was identified by standard DNA miniprep procedures. Digestion of the recombinant adenovirus DNA with FseI and AscI confirmed the presence of BMP-7 DNA. The recombinant adenovirus miniprep DNA was transformed into *E. coli* DH10B competent cells (Life Technologies, Inc., Gaithersburg, Md., USA), and DNA was prepared therefrom.

Approximately 5 μg of recombinant adenoviral DNA was digested with PacI enzyme (New England Biolabs) for 3 hours at 37° C. in a reaction volume of 100 μl containing 20-30 U of PacI. The digested DNA was extracted twice with an equal volume of phenol/chloroform and precipitated with ethanol. The DNA pellet was resuspended in 10 μl distilled water. A T25 flask of QBI-293A cells (Quantum Biotechnologies, Inc., Montreal, Canada), inoculated the day before and grown to 60-70% confluence, were transfected with the PacI digested DNA. The PacI-digested DNA was diluted up to a total volume of 50 μl with sterile HBS (150 mM NaCl, 20 mM HEPES). In a separate tube, 20 μl of 1 mg/ml N-[1-(2,3-Dioleoyloxy)propyl]-N,N,N-trimethyl-ammonium methyl-sulfate (DOTAP; Boehringer Mannheim) was diluted to a total volume of 100 μl with HBS. The DNA was added to the DOTAP, mixed gently by pipeting up and down, and left at room temperature for 15 minutes. The media was removed from the 293A cells and washed with 5 ml serum-free MEM-alpha (Life Technologies, Gaithersburg, Md., USA) containing 1 mM sodium pyruvate (Life Technologies), 0.1 mM MEM non-essential amino acids (Life Technologies) and 25 mM HEPES buffer (Life Technologies). 5 ml of serum-free MEM was added, and the cells were held at 37° C. The DNA/lipid mixture was added drop-wise to the flask, mixed gently, and incubated at 37° C. for 4 hours. After 4 hours the media containing the DNA/lipid mixture was aspirated off and replaced with 5 ml complete MEM containing 5% fetal bovine serum. The transfected cells were monitored for GFP expression and formation of foci (viral plaques).

Seven days after transfection of 293A cells with the recombinant adenoviral DNA, cells expressing GFP started to form foci. The crude viral lysate was collected with a cell scraper to collect the cells. The lysate was transferred to a 50 ml conical tube. To release most of the virus particles from the cells, three freeze/thaw cycles were done in a dry ice/ethanol bath and a 37° C. waterbath.

Ten 10-cm plates of nearly confluent (80-90%) 293A cells were set up 20 hours prior to infection. The crude lysate was amplified (primary amplification) to obtain a working stock of BMP-7 recombinant Ad5 virus (rAd5 virus) lysate. 200 ml of crude rAd5 virus lysate was added to each 10-cm plate, and the plates were monitored for 48 to 72 hours looking for cytopathic effects (CPE) under the white light microscope and expression of GFP under the fluorescent microscope. When all of the cells showed CPE, this first stock lysate was collected, and freeze/thaw cycles were performed as described above.

Secondary (2nd) amplification of BMP-7 rAd5 virus was obtained from twenty 15-cm tissue culture dishes of 80-90% confluent 293A cells. All but 20 ml of 5% MEM media was removed, and each dish was inoculated with 300-500 ml of first amplified rAd5 virus lysate. After 48 hours the cells were lysed from virus production, the lysate was collected into 250 ml polypropylene centrifuge bottles, and the rAd5 virus was purified.

NP-40 detergent was added to a final concentration of 0.5% to the bottles of crude lysate to lyse all cells. Bottles were placed on a rotating platform for 10 minutes and agitated as fast as possible. The debris was pelleted by centrifugation at 20,000× G for 15 minutes. The supernatant was transferred to 250-ml polycarbonate centrifuge bottles, and 0.5 volume of 20% PEG8000/2.5M NaCl solution was added. The bottles were shaken overnight on ice. The bottles were centrifuged at 20,000× G for 15 minutes, and the supernatants were discarded into a bleach solution. A white precipitate (precipitated virus/PEG) formed in two vertical lines along the walls of the bottles on either side of the spin mark. Using a sterile cell scraper, the precipitate from 2 bottles was resuspended in 2.5 ml PBS. The virus solution was placed in 2-ml microcentrifuge tubes and centrifuged at 14,000× G in a microcentrifuge for 10 minutes to remove any additional cell debris. The supernatants from the 2-ml microcentrifuge tubes were transferred into a 15-ml polypropylene snapcap tube and adjusted to a density of 1.34 g/ml with CsCl. The volume of the virus solution was estimated, and 0.55 g/ml of CsCl added. The CsCl was dissolved, and 1 ml of this solution weighed. The solution was transferred to polycarbonate, thick-walled, 3.2 ml centrifuge tubes (Beckman) and spun at 348,000× G for 3-4 hours at 25° C. The virus formed a white band. Using wide-bore pipette tips, the virus band was collected.

The virus recovered from the gradient included a large amount of CsCl, which must be removed before it can be used on cells. Pharmacia PD-10 columns prepacked with Sephadex® G-25M (Pharmacia) were used to desalt the virus preparation. The column was equilibrated with 20 ml of PBS. The virus was loaded and allowed to run into the column. 5 ml of PBS was added to the column, and fractions of 8-10 drops collected. The optical density of a 1:50 dilution of each fraction was determined at 260 nm on a spectrophotometer, and a clear absorbance peak was identified. Peak fractions were pooled, and the optical density (OD) of a 1:25 dilution was determined. OD was converted into virus concentration using the formula (OD at 260 nm)(25)($1.1 \times 10^{12}$)=virions/ml.

To store the virus, glycerol was added to the purified virus to a final concentration of 15%, mixed gently and stored in aliquots at −80° C.

Example 3

Construction of the Ad5 Adenovirus Vector Having Human BMP-7 Insert

The nucleic acid and amino acid sequences of the human BMP-7 are available on GenBank database under the accession number AL122058.

The codon-optimized human BMP-7 open reading frame ("ORF") consists of 1296 bp (SEQ ID NO: 14) and encodes a 431 amino acids polypeptide (SEQ ID NO: 15).

To prepare adenovirus vectors according to the method described in the Example 2, the codon-optimized nucleotide sequence SEQ ID NO: 14 of the human BMP-7 polypeptide is used as starting material.

The recombinant Ad5 viruses, comprising as insert the codon-optimized nucleotide sequence of human BMP-7, are harvested, purified and stored as described in Example 2.

Example 4

Construction of the Ad5 Adenovirus Vector Having Canine BMP-7 Insert

The nucleic acid and amino acid sequences of the canine BMP-7 are available on GenBank database under the accession number XM_862341.

The codon-optimized canine BMP-7 open reading frame ("ORF") consists of 1296 bp (SEQ ID NO: 2) and encodes a 431 amino acids polypeptide (SEQ ID NO: 3).

To prepare adenovirus vectors according to the method described in the Example 2, the codon-optimized nucleotide sequence SEQ ID NO: 2 of the canine BMP-7 polypeptide is used as starting material.

The recombinant Ad5 viruses, comprising as insert the codon-optimized nucleotide sequence of canine BMP-7, are harvested, purified and stored as described in Example 2.

Example 5

Construction of the Ad5 Adenovirus Vector Having Feline BMP-7 Insert

The nucleic acid and amino acid sequences of the feline BMP-7 are those described in Example 1.

The codon-optimized feline BMP-7 open reading frame ("ORF") consists of 1296 bp (SEQ ID NO: 18) and encodes a 431 amino acids polypeptide (SEQ ID NO: 19).

To prepare adenovirus vectors according to the method described in the Example 2, the codon-optimized nucleotide sequence SEQ ID NO: 18 of the feline BMP-7 polypeptide is used as starting material (pPB770 plasmid of the Example 1).

The recombinant Ad5 viruses, comprising as insert the codon-optimized nucleotide sequence of feline BMP-7, are harvested, purified and stored as described in Example 2.

Example 6

Construction of the Ad5 Adenovirus Vector Having Equine BMP-7 Insert

The nucleic acid and amino acid sequences of the equine BMP-7 are available on GenBank database under the accession number XM_001489796.

The equine BMP-7 open reading frame ("ORF") consists of 1296 bp (SEQ ID NO: 10) and encodes a 431 amino acids polypeptide (SEQ ID NO: 16).

To prepare adenovirus vectors according to the method described in the Example 2, the nucleotide sequence SEQ ID NO: 10 of the equine BMP-7 polypeptide is used as starting material.

The recombinant Ad5 viruses, comprising as insert the nucleotide sequence of equine BMP-7, are harvested, purified and stored as described in Example 2.

Example 7

Construction of the CAV-2 Adenovirus Vector Having Canine BMP-7 Insert

Madin and Darby canine kidney (MDCK) cell suspensions are seeded in MEM supplemented with 7.5% fetal bovine serum, sodium pyruvate (1 mM final), glutamine (2 mM final), penicillin (50 U/ml), streptomycin (50 mg/ml) and non essential amino acids (0.1 mM final). Confluent cells are infected with serial dilutions of a CAV2 vaccine strain (U.S. Pat. No. 6,090,393; U.S. Pat. No. 6,156,567) and cultured under a 0.6% agarose overlay. CAV2 is subjected to several rounds of plaque purification.

In order to identify a DNA fragment containing the entire E3 region, purified CAV2 DNA aliquots are digested with BamHI, BglI, HindII, HindIII and PstI and analyzed by Southern blotting as described in Sambrook J. et al., Molecular cloning: a laboratory manual, $2^{nd}$ edition Cold Spring Harbor, N.Y.: Cold Spring Laboratory, 1989. Couples of primers LF189 SEQ ID NO: 29 (21 mer) 5'-TCAGTCAT-AGCCATCGACAGA-3'/LF190 SEQ ID NO: 30 (21 mer) (5'-GTGCTGGCTGGCACGGGCATT-3') and LF191 SEQ ID NO: 31 (21 mer) (5'-ATGTCCACCAAAGTCCCCTCT-3')/LF192 SEQ ID NO: 32 (21 mer) (5'-CCCGGGGCGTCG-TATGGATAT-3') are designed to generate molecular probes specific of the 3' end of the CAV2 PVIII sequence or of the 5' end of the CAV2 fiber gene, respectively. The HindIII fragment A (4.0 Kbp), corresponding to the largest isolated restriction fragment recognized by both PVIII and Fiber probes is cloned into the vector pBluescript SK+ (Stratagene), generating pLF027. Sequencing of the entire pLF027 E3 insert is performed on both strands.

In order to facilitate subsequent cloning strategies, a DNA linker (SEQ ID NO: 33) (24 mer) 5'-GATACGCGTTCCATT-AGCAGATCT-3', containing unique BglII and MluI restriction sites, is introduced into the CAV2 E3 region by a double round PCR amplification procedure. Initial PCR amplifications is performed using pLF027 DNA as template and the following primer couples [LF327 SEQ ID NO: 34 (24 mer) 5'-GGACACCTTTCTGATCAGTTCATT-3'/LF324 SEQ ID NO: 35 (45 mer) 5'-GATACGCGTTCCATTAGCA-GATCTTTGAGGGGCCTGGAAATAGGC-3'] and [LF326 SEQ ID NO: 36 (24 mer) 5'-GGTTGTGTGGAAGAC-CCGGGGGCG-3'/LF325 SEQ ID NO: 37 (45 mer) 5'-AG-ATCTGCTAATGGAACGCGTATCGCTGC-CCCCACAGTACAGCAA-3'], to generate two partially overlapping DNA fragments of 838 bp and 956 bp, respectively. The second round of PCR amplification is performed in the presence of both partially overlapping purified DNA fragments and both external primers LF327 and LF326. The purified 890 bp PstI/AatII fragment is ligated with the 6069 bp PstI/AatII DNA fragment of pLF027, generating pLF047A. In order to delete part of the CAV2 E3 region, a 428 bp deletion is engineered downstream (3)' of the pLF047A MluI site. A 537 bp DNA fragment is generated by PCR using the pLF027 template and the primers pair LF361 SEQ ID NO: 38 (38 mer) 5'-CTAGTCATCTTAACGCGTGTCCTCAA-CATCACCCGCGA-3'/LF334 SEQ ID NO: 39 (21 mer) 5'-CTTGCTTGTTATTAAAAAAAG-3'. The purified 551 bp MluI/AatI DNA fragment is ligated with the 6944 bp MluI/AatII DNA fragment of pLF047A, generating pLF086. In order to engineer a larger deletion within the E3 region, a PCR amplification is implemented using pLF027 DNA as a template and primers LF437 SEQ ID NO: 40 (33 mer) 5'-ATCT-TAACGCGTCCCTCAGCCTTCTAATGGGAC-3' and LF334. The 287 bp MluI/SmaI amplified DNA fragment is ligated with the 6079 bp MluI/SmaI DNA fragment of pLF086, generating pLF095.

With the objective to reduce as much as possible the size of the expression cassette, a truncated hCMV IE promoter is generated by PCR using hCMV DNA as a template and primers LF172 SEQ ID NO: 41 (31 mer) 5'-ATCG-TAAAGCTTAATGTCGTAATAACCCCGC-3' and LF159 SEQ ID NO: 42 (32 mer) 5'-TCTACTGCAGCCGGTGTCT-TCTATGGAGGTCA-3'. The purified HindIII/PstI 166 bp DNA fragment is cloned into the corresponding sites of the pCAT basic vector (Promega) to generate pLF022. To further reduce the size of the polyadenylation cassette, a 170 bp DNA fragment is amplified by PCR using primers LF377 SEQ ID NO: 43 (24 mer) 5'-TCTTCGCCCCCGTTTTCACCATGG-3' and LF378 SEQ ID NO: 44 (34 mer) 5'-ATCACGCCGCG-GCTTAAAAAAATTACGCCCCGCC-3' and pLF022 DNA as template. The purified DNA fragment is Klenow-treated and digested with NcoI before being ligated with the 3655 bp NcoI/BsaBI DNA fragment of pLF022, generating pLF062. In order to improve the expression of the recombinant antigen after the onset of CAV2 replication, the human adenovirus 2 (hAd2) tripartite leader (TPL) is introduced downstream of the hCMV IE promoter in pLF062. Oligonucleotides SPH6Etr1 SEQ ID NO: 45 (71 mer) 5'-AATTCGGTAC-CAAGCTTCTTTATTCTATACT-TAAAAAGTGAAAATAAATACAAAGGT TCT-TGACTCTCTTC-3', SPH6Etr2 SEQ ID NO: 46 (70 mer) 5'-CGCATCGCTGTCTGCGAGGGCCAGCTGT-TGGGCTCGCGGTTGAGGACAAACTCTTCG CGGTCTTTCCAGT-3', SPH6Etr3 SEQ ID NO: 47 (70 mer) 5'-ACTCTTGGATCGGAAACCCGTCGGCCTC-CGAACGTACTCCGCCACCGAGGGACCTG AGC-GAGTCCGCATC-3', SPH6Etr4 SEQ ID NO: 48 (60 mer) 5'-GACCGGATCGGAAAACCTCTCGAGAAAG-GCGTCTAACCAGTCACAGTCGCAAGCCC GGGT-3', SPH6Etr5 SEQ ID NO: 49 (51 mer) 5'-CTTTGTATT-TATTTTCACTTTTTAAGTATAGAATAAA-GAAGCTTGGTACCG-3', SPH6Etr6 SEQ ID NO: 50 (72 mer) 5'-GAAGAGTTTGTCCTCAACCGCGAGC-CCAACAGCTGGCCCTCGCAGACAGCGATGCG GAA-GAGAGTCAAGAAC-3', SPH6Etr7 SEQ ID NO: 51 (73 mer) 5'-GCTCAGGTCCCTCGGTGGCGGAGTACGT-TCGGAGGCCGACGGGTTTCCGATCCAAG AGTACTGGAAAGACCGC-3', and SPH6Etr8 SEQ ID NO: 52 (75 mer) 5'-CTAGACCCGGGCTTGCGACTGT-GACTGGTTAGACGCCTTTCTCGAGAGGTTTTCCGA TCCGGTCGATGCGGACTC-3' are kinased and annealed and the 271 bp product was gel purified. A 220 bp DNA fragment containing the entire hAd2 TPL flanked by PstI and XbaI restriction sites is generated by PCR using primers LF394 SEQ ID NO: 53 (36 mer) 5'-ATCGTCCTGCA-GACTCTCTTCCGCATCGCTGTCTGC-3' and LF395 SEQ ID NO: 54 (29 mer) 5'-GCTCTAGACTTGCGACTGT-GACTGGTTAG-3' and the aforementioned gel purified annealed oligonucleotides as template, is subsequently ligated with the 3800 bp PstI/XbaI pLF062 fragment, to generate pLF066. In order to further reduce the size of the expression cassette, the 3936 bp SacI/PstI fragment of pLF066 is ligated with annealed oligonucleotides LF397 SEQ ID NO: 55 (20 mer) 5'-CGTTTAGTGAACCGTCTGCA-3' and LF398 SEQ ID NO: 56 (20 mer) 5'-GACGGTTCAC-TAAACGAGCT-3', to generate pLF069 in which the 5'UTR of the hCMV IE promoter is replaced by the hAd2TPL.

To increased expression canine BMP-7, a codon-optimized cDNA sequence is chemically synthesized based on Genbank sequence P34819 and subsequently subcloned into pLF069 to generate pLF1000. The pLF1000 plasmid contains the codon-optimized canine BMP-7 cDNA in the rightward orientation in the pLF069 backbone. To further reduce the size of the polyadenylation cassette, a 160 bp DNA fragment is amplified using primers M13R SEQ ID NO: 57 (18 mer) 5'-GTAAAAACGACGGCCAGT-3' and LF409 SEQ ID NO: 58 (33 mer) 5'-ATCGTCCCGCGGAATTGTTGTTGT-TAACTTGTT-3' and pCAT Basic DNA as template. The amplified 145 bp KspI/BamHI DNA fragment is ligated with the 5002 bp KspI/BamHI DNA fragment of pLF1000, generating pLF1001, which contains the codon-optimized canine BMP7 cDNA flanked by a shorter polyadenylation cassette.

5 µg of the purified CAV2 DNA are transfected into MDCK cells using Lipofectamine as described by the manufacturer (Gibco Lifesciences). After 24 hours of incubation at 37° C., the serum free medium is removed and replaced by the supplemented MEM medium. The culture is incubated at 37° C. for 8 days with supplemented MEM medium being added to it on the third day. No cytopathic effect (CPE) could be evidenced during this incubation. On day 8 the transfected MDCK cells are harvested. After sonication on ice, 2 ml of the transfected culture are used to infect a confluent MDCK monolayer. Plaques appear after 5 days with a typical yield of at least 2,000 pfu/10 µg of purified DNA.

The pLF1001 DNA fragment containing the canine BMP-7 cDNA in the rightward orientation flanked by the aforementioned expression regulatory sequences is purified by GeneClean and resuspended to a concentration of 10 ng/ml and subsequently, recombined in vitro with purified CAV2 DNA in the presence of Lipofectamine as described by the manufacturer.

The CAV2 DNA/liposome complexes are gently mixed with supplemented MEM medium (serum free) before being transfected into MDCK cells as described above. Plaques are screened for recombinant viruses by the filter hybridization method. Briefly, plaques were transferred onto a nitrocellulose filter, then transferred from the original filters to replica filters. The original filters are hybridized with a specific DNA probe to identify plaques containing the canine BMP-7 gene. Recombinant virus is retrieved from the corresponding plaques on the replica filter.

Example 8

Animal Experiment and Results

A study was conducted in sheep to demonstrate the ability of BMP-7 gene therapy to interfere with the progression of post-traumatic osteoarthritis.

14 adult, 1.5-5.0 year old, 40-70 kg, castrated male or non-gravid female Arcott sheep were allocated randomly into 2 groups (Group 1 and Group 2).

Under general anesthesia and using aseptic technique, all sheep received standardized 30 MPa impact injuries to both (left and right) medial femoral condyles by a 3 cm minimally invasive arthrotomy. Briefly, a 2 cm long infrapatellar arthrotomy and partial resection of the fat pad was used to expose the medial femoral condyle of both knee joints. Using a hand-held spring loaded impact device equipped with an 6 mm diameter tip and an in line force transducer, two overlapping 30 MPa impact injuries were made 1 cm distal to the linea terminalis. It was day 0 (D0) of the study.

At D7, the sheep were sedated with diazepam (10 mg/kg) and ketamine (3-5 mg/kg) to allow the following treatments to be administered. The sheep of Group 1 received a dose of 1 mL of murine BMP-7 Ad5 vector (example 2) ($10^9$ virus particles/mL) into the stifle joint of one knee. The administration was done intra-articularly with a syringe and needle into the femoropatellar joint with the animal sedated and held upright with the limb extended. Injection was done after synovial fluid (1 mL) was collected. The other knee was not treated. FIG. 1 gives information about the treatment administered on each knee of each animals of Group 1. The sheep of Group 2 did not receive any treatment and remained as control.

Serum and synovial fluid were harvested on D0, D14, D21, D28, D60 and D90. On D90, tissues were also collected for macroscopic examination and histology.

Stall side clinical signs were recorded once daily during the experiment period. Lameness was recorded daily on a scale from 0-5 where 0 is normal and 5 is non-weight bearing. Animals with a score of >2/5 for more than 7 days will be examined and an arthrocentesis performed to rule out sepsis. Animals with a score of >3/5 for 7 days will be administered analgesics (fentanyl patch 1 mg/kg 5 days) until the lameness improves or the animal is removed from the study.

One animal of Group 1 was euthanized during experiment due to septicemia and pneumonia.

FIG. 1 provides macroscopic data at necropsy on D90. This figure shows the beneficial effect of the treatment, demonstrated using macroscopic endpoint (p<0.05).

FIG. 2 provides pictures of the left and right knee of one of the animals of Group 1, Y13.

Figure 3:
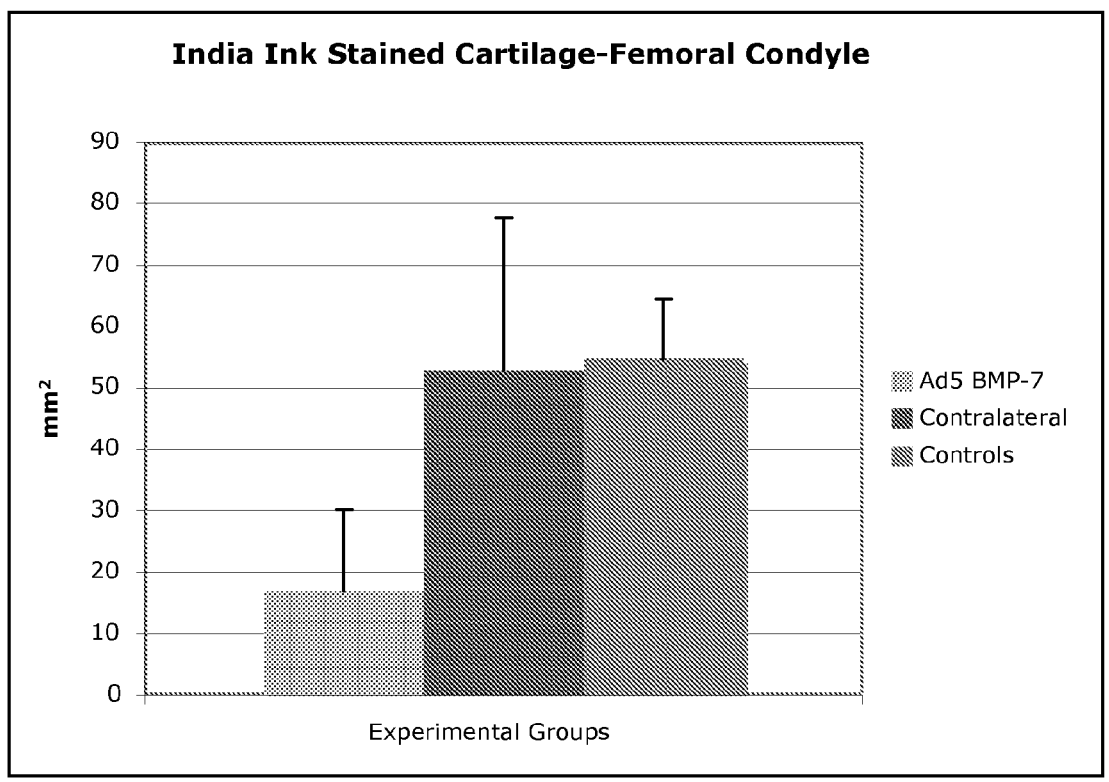
FIG. 3 provides cartilage preservation after injury expressed in square-millimeter of cartilage surface roughening as measured by India ink retention for BMP-7 treated joints and contralateral non-treated joints of animals of group 1 and for non-treated animals of group 2.

FIG. 3 provides quantitative macroscopic observations and shows a clear improvement in cartilage damage between treated and control animals (p<0.001). Macroscopic indicators of cartilage preservation after injury included reduction in surface roughening as measured by India ink retention. Briefly, the area of abnormal cartilage was delineated using India ink staining. Stained areas were calculated by tracing ink uptake onto plastic film and area measurement with semi-automated morphometry software (Northern Eclipse™).

Figure 4:
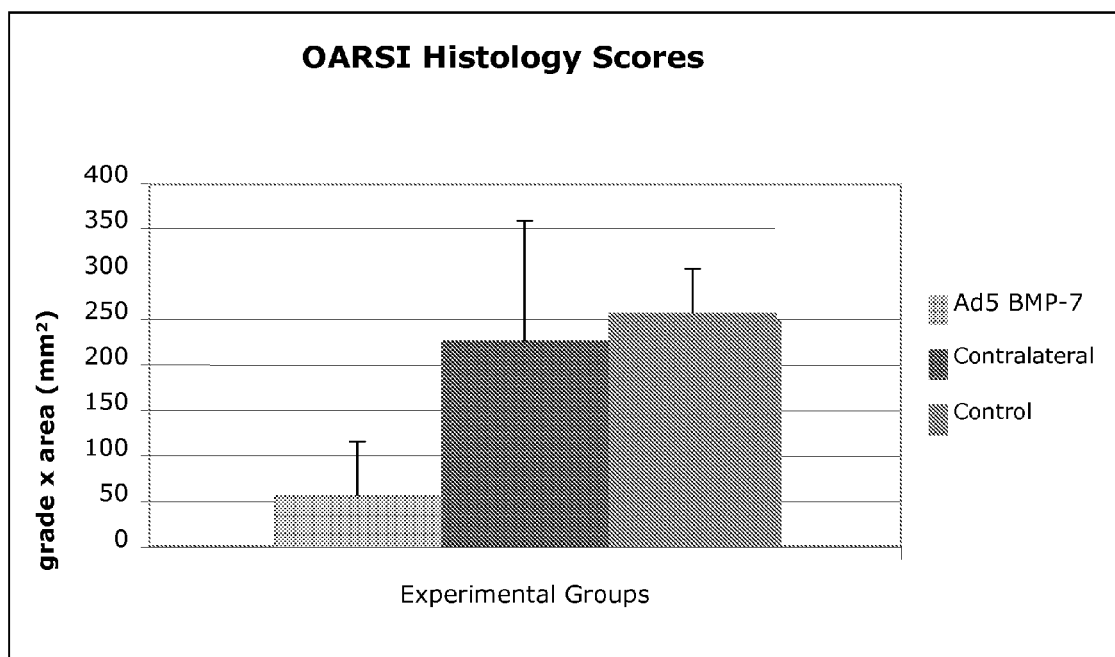
FIG. 4 provides quantitative histological observations using OARSI scoring with assigning a grade to the depth of cartilage erosion and a stage to the India ink stained area (expressed in square-millimeter of cartilage surface roughening as measured by India ink retention) for BMP-7 treated joints and contralateral non-treated joints of animals of group 1 and for non-treated animals of group 2.

FIG. 4 provides quantitative histological observations using OARSI scoring with assigning a grade to the depth of cartilage erosion and a stage to the India ink stained area (about OARSI score see Pritzker K P H et al., Osteoarthritis and Cartilage, 2006, 14: 13-29). In a linear model statistical analysis, treated Group 1 joints were improved over Group 2 controls (p<0.0007) and Group 1 contralateral joints (p<0.004).

Reduced disease progression in treated joints compared to contralateral joints and to the joints of control animals were supported by the absence of collagen degradation CII3/4 short epitope (hallmarks of cartilage degradation and OA progression) at distant sites from the experiment defect;

- 7 out of 8 control (group 2) joints had evidence of progressive degeneration as indicated by the presence of CII3/4 short epitope.
- 3 out of 4 (examined) contralateral joints had CII3/4 short staining distant from the injury site.
- 0 out of 7 Ad5 BMP-7 treated knee joints had evidence of C3/4 short epitope staining distant from the injury site.

Reduced disease progression in treated joints were also supported by TUNEL staining (to determine if treatment blocked programmed cell death after mechanical injury to cartilage; about TUNEL staining see Echigo R. et al., J. Vet. Med. Sci., 2006, 68(8): 899-902):

- Of the 7 Ad5 BMP-7 treated joints, 7 were positive at the injury site, 2 were negative in the surrounding cartilage and the remaining 5 had reduced TUNEL staining distant from the experimental impact zone.
- All contralateral joints had TUNEL positivity both in the defect sites and in the surrounding cartilage.
- All controls had TUNEL positivity both in the defect sites and in the surrounding cartilage.

Evidence of improvement in Ad5 BMP-7 transfected joints over contralateral joint has been obtained with a lack of OA progression and cell loss indicating reduced disease progression in treated joints. This data clearly demonstrates the beneficial effect of BMP-7 adenovirus-based gene therapy in a very severe experimental model of osteoarthritis.

Example 9

Construction of the Ad5 Adenovirus Vector Having Equine IL10 Insert

The nucleic acid and amino acid sequences of the equine interleukine-10 (IL10) are available on GenBank database under the accession number U38200.

The equine IL10 open reading frame ("ORF") consists of 537 bp (SEQ ID NO: 59) and encodes a 178 amino acids polypeptide (SEQ ID NO: 60).

To prepare adenovirus vectors according to the method described in the Example 2, the nucleotide sequence SEQ ID NO: 59 is used as starting material.

The recombinant Ad5 viruses, comprising as insert the nucleotide sequence of equine IL10, are harvested, purified and stored as described in Example 2.

Example 10

Construction of the Ad5 Adenovirus Vector Having Canine IL10 Insert

The nucleic acid and amino acid sequences of the canine interleukin-10 (IL10) are available on GenBank database under the accession number XM_850467.1.

The canine IL10 ORF consists of 540 bp (SEQ ID NO: 61) and encodes a 179 amino acids polypeptide (SEQ ID NO: 62).

To prepare adenovirus vectors according to the method described in the Example 2, the nucleotide sequence SEQ ID NO: 61 is used as starting material.

The recombinant Ad5 viruses, comprising as insert the nucleotide sequence of canine IL10, are harvested, purified and stored as described in Example 2.

Example 11

Construction of the Ad5 Adenovirus Vector Having Feline IL10 Insert

The nucleic acid and amino acid sequences of the feline interleukin-10 (IL10) are available on GenBank database under the accession number NM_001009209.1.

The feline IL10 ORF consists of 537 bp (SEQ ID NO: 63) and encodes a 178 amino acids polypeptide (SEQ ID NO: 64).

To prepare adenovirus vectors according to the method described in the Example 2, the nucleotide sequence SEQ ID NO: 63 is used as starting material.

The recombinant Ad5 viruses, comprising as insert the nucleotide sequence of feline IL10, are harvested, purified and stored as described in Example 2.

Example 12

Construction of the Ad5 Adenovirus Vector Having Human IL10 Insert

The nucleic acid and amino acid sequences of the human interleukine-10 (IL10) are available on GenBank database under the accession number NM_000572.2.

The human IL10 ORF consists of 537 bp (SEQ ID NO: 65) and encodes a 178 amino acids polypeptide (SEQ ID NO: 66).

To prepare adenovirus vectors according to the method described in the Example 2, the nucleotide sequence SEQ ID NO: 65 is used as starting material.

The recombinant Ad5 viruses, comprising as insert the nucleotide sequence of human IL10, are harvested, purified and stored as described in Example 2.

Example 13

Construction of the Ad5 Adenovirus Vector Having Viral IL10 Insert

The nucleic acid and amino acid sequences of the viral interleukine-10 (IL10) are available on GenBank database under the accession number AF182315.

The viral IL10 ORF consists of 528 bp (SEQ ID NO: 67) and encodes a 175 amino acids polypeptide (SEQ ID NO: 68).

To prepare adenovirus vectors according to the method described in the Example 2, the nucleotide sequence SEQ ID NO: 67 is used as starting material.

The recombinant Ad5 viruses, comprising as insert the nucleotide sequence of viral IL10, are harvested, purified and stored as described in Example 2.

The invention is further described by the following numbered paragraphs:

1. A method of treating a mammalian subject suffering from osteoarthritis, comprising, administering intra-articularly to said mammalian subject a therapeutically effective amount of a composition comprising at least one pharmaceutically or veterinarily acceptable carrier, excipient, or vehicle and recombinant adenovirus vectors containing a nucleic acid sequence encoding a BMP-7 polypeptide operatively linked to a promoter, wherein the BMP-7 polypeptide is expressed in vivo in the mammalian subject.

2. The method according to paragraph 1, wherein the recombinant adenovirus vectors are human adenoviruses.

3. The method according to paragraph 2, wherein the human adenoviruses are human adenoviruses type 5 (hAd5).

4. The method according to paragraph 3, wherein the human adenoviruses type 5 (hAd5) are PEGylated.

5. The method according to paragraph 1, wherein the recombinant adenovirus vectors are canine adenoviruses.

6. The method according to paragraph 5, wherein the canine adenoviruses are canine adenoviruses type 2 (CAV2).

7. The method according to paragraph 1, wherein the mammalian subject is selected from the group consisting of human, canidae, equidae and felidae.

8. The method according to paragraph 1 wherein the mammalian subject is a dog, a bitch or a puppy.

9. The method according to paragraph 1 wherein the mammalian subject is a cat or a kitten.

10. The method according to paragraph 1 wherein the mammalian subject is a horse, a mare or a foal.

11. The method according to paragraph 1, wherein the BMP-7 polypeptide is selected from the group consisting of a pre-pro BMP-7 polypeptide, a pro-BMP-7 polypeptide, and a mature BMP-7 polypeptide.

12. The method according to paragraph 1, wherein the BMP-7 polypeptide is selected from the group consisting of a canine pre-pro BMP-7 polypeptide, a canine pro-BMP-7 polypeptide, a canine mature BMP-7 polypeptide, a feline pre-pro BMP-7 polypeptide, a feline pro-BMP-7 polypeptide, a feline mature BMP-7 polypeptide, an equine pre-pro BMP-7 polypeptide, an equine pro-BMP-7 polypeptide, an equine mature BMP-7 polypeptide, a human pre-pro BMP-7 polypeptide, a human pro-BMP-7 polypeptide, and a human mature BMP-7 polypeptide.

13. The method according to paragraph 1, wherein the nucleic acid sequence encoding the BMP-7 polypeptide is selected from the group consisting of SEQ ID NO: 1, SEQ ID NO: 2, SEQ ID NO: 10, SEQ ID NO: 13, SEQ ID NO: 14, SEQ ID NO: 17, SEQ ID NO: 18, and fragments, variants, derivatives and homologs thereof that encode polypeptides having BMP-7 activity.

14. The method according to paragraph 1, wherein the BMP-7 polypeptide has an amino acid sequence selected from the group consisting of SEQ ID NO: 3, SEQ ID NO: 15, SEQ ID NO: 16, SEQ ID NO: 19 and fragments, variants, derivatives and homologs thereof having BMP-7 activity.

15. The method according to paragraph 1, wherein the BMP-7 polypeptide comprises a signal peptide.

16. The method according to paragraph 15, wherein the signal peptide is selected from the group consisting of the BMP-7 signal sequence, the IGF-1 signal sequence, and the tPA signal sequence.

17. The method according to paragraph 15, wherein the signal peptide is encoded by a nucleotide sequence selected from the group consisting of SEQ ID NO: 4, SEQ ID NO: 6, SEQ ID NO: 8, SEQ ID NO: 11, and fragments, variants, derivatives and homologs thereof that encode peptides having signal peptide activity.

18. The method according to paragraph 15, wherein the signal peptide has an amino acid sequence selected from the group consisting of SEQ ID NO: 5, SEQ ID NO: 7, SEQ ID NO: 9, SEQ ID NO: 12, and fragments, variants, derivatives and homologs thereof having signal peptide activity.

19. The method according to paragraph 1 wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatin kinase gene promoter.

20. The method according to paragraph 1 wherein the BMP-7 polypeptide is selected from the group consisting of a canine pre-pro BMP-7 polypeptide, a canine pro-BMP-7 polypeptide, a canine mature BMP-7 polypeptide and the promoter is a canine synoviocyte specific promoter.

21. The method according to paragraph 1 wherein the nucleic acid sequence encoding the BMP-7 polypeptide is selected from the group consisting of SEQ ID NO: 1, SEQ ID NO: 2, and fragments, variants, derivatives and homologs thereof that encode polypeptides having BMP-7 activity and the promoter is a canine synoviocyte specific promoter.

22. A pharmaceutical composition comprising recombinant adenovirus vectors according to anyone of paragraphs to 1 to 21, and at least one pharmaceutically or veterinarily acceptable carrier, excipient, or vehicle.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating a mammalian subject suffering from osteoarthritis, comprising administering intra-articularly to said mammalian subject a therapeutically effective amount of a composition comprising at least one pharmaceutically or veterinarily acceptable carrier, excipient, or vehicle and recombinant adenovirus vectors comprising a polynucleotide encoding a BMP-7 polypeptide having the sequence as set forth in SEQ ID NO: 3 operatively linked to a promoter.

2. The method of claim 1, wherein the BMP-7 polynucleotide has the sequence as set forth in SEQ ID NO: 2.

3. The method according to claim 1, or 2, wherein the recombinant adenovirus vectors are human adenoviruses.

4. The method according to claim 3, wherein the human adenoviruses are human adenoviruses type 5 (hAd5).

5. The method according to claim 4, wherein the human adenoviruses type 5 (hAd5) are PEGylated.

6. The method according to claim 1, or 2, wherein the recombinant adenovirus vectors are canine adenoviruses.

7. The method according to claim 6, wherein the canine adenoviruses are canine adenoviruses type 2 (CAV2).

8. The method according to claim 1, or 2, wherein the mammalian subject is selected from the group consisting of human, canidae, equidae and felidae.

9. The method according to claim 1, or 2, wherein the mammalian subject is a dog, a bitch or a puppy.

10. The method according to claim 1, or 2, wherein the mammalian subject is a cat or a kitten.

11. The method according to claim 1, or 2, wherein the mammalian subject is a horse, a mare or a foal.

12. The method according to claim 1, or 2, wherein the promoter is selected from the group consisting of a CMV IE promoter, a RSV promoter, an HSV-1 TK promoter, a SV40 early promoter, a SV40 late promoter, an adenovirus major late promoter, a phosphoglycerate kinase gene promoter, a metallothionein gene promoter, an α-1 antitrypsin gene promoter, an albumin gene promoter, a collagenase gene promoter, an elastase I gene promoter, a β-actin gene promoter, a β-globin gene promoter, a γ-globin gene promoter, an α-fetoprotein gene promoter, and a muscle creatine kinase gene promoter.

* * * * *

SEQUENCE LISTING

```
<160> NUMBER OF SEQ ID NOS: 69

<210> SEQ ID NO 1
<211> LENGTH: 1296
<212> TYPE: DNA
<213> ORGANISM: Canis sp.

<400> SEQUENCE: 1
```

```
atgcacgtgc gctcgccctg cgccgcggcg ccccgcagct tcgtggcgct ctgggcgccc      60
ctgctcctgc tgcgctccgc cctggccgac ttcagcctgg acaacgaggt gcactcgagc     120
ttcatccacc ggcgcctccg cagccaggag cggcgggaga tgcagcgcga gatcctctct     180
atcctgggct tgccccaccg cccgcgcccg cacctccagg gcaagcacaa ctcggcgccc     240
atgttcatgc tggacctgta caatgccatg gcggtggagg agggcggcgg gcccgacggc     300
cagggcttct cctaccccta caaggccgtc ttcagcaccc agggcccccc tctggccagc     360
ctgcaagaca gccacttcct caccgacgcc gacatggtca tgagcttcgt caacctcgtg     420
gagcatgaca aagagttctt ctatccacgt taccaccacc gggagttccg gttcgatctc     480
tccaagatcc agagggggga agctgtgact gcagccgaat tccggatcta caaggactac     540
attcgggagc gcttcgacaa cgagacgttc cggatcagcg tttaccaggt gctgcaggag     600
cacttgggca gggagtcaga cctgttcctg ctggacagcc gcaccctctg gcctcggag      660 gagggctggc tggtgttcga catcacagcc accagcaacc actgggtggt caacccacga     720
cacaacctgg gcctgcagct ctgcgtggag accttggacg gcagagcat caaccccaag      780 ttggcgggcc tgatcgggcg gcacgggccc cagaacaagc agcccttcat ggtggccttc     840
ttcaaggcca cggaagtcca cctccgcagc acgcgctcca cgggcgccaa gcagcgcagc     900
cagaaccgct ccaagacgcc caagaaccag gaagccctgc gggtggccaa cgtcgcagaa     960
aacagcagca cgaccagag gcaggcctgc aagaagcacg aactgtacgt cagcttccgc     1020
gatctgggct ggcaggactg gatcatcgct cccgaaggct atgccgctta ctactgtgag     1080
ggggagtgtg ccttccccct gaactcctac atgaacgcca ccaaccacgc catcgtgcag     1140
acgctggtcc acttcatcaa ccccgaaacg gtgcccaagc catgctgtgc ccccactcag     1200
ctcaacgcca tctctgtcct ctacttcgac gacagctcca acgtcatcct gaagaaatac     1260
agaaacatgg tcgtccgagc ctgtggctgc cactag                               1296
```

<210> SEQ ID NO 2
<211> LENGTH: 1296
<212> TYPE: DNA
<213> ORGANISM: Artificial Sequence
<220> FEATURE:
<223> OTHER INFORMATION: Description of Artificial Sequence: Synthetic construct

<400> SEQUENCE: 2

```
atgcatgtgc gcagcccgtg cgcggcggcg ccgcgcagct ttgtggcgct gtgggcgccg      60
ctgctgctgc tgcgcagcgc gctggcggat tttagcctgg ataacgaagt gcatagcagc     120
tttattcatc gccgcctgcg cagccaggaa cgccgcgaaa tgcagcgcga aattctgagc     180
attctgggcc tgccgcatcg cccgcgcccg catctgcagg gcaaacataa cagcgcgccg     240
atgtttatgc tggatctgta taacgcgatg gcggtggaag aaggcggcgg cccggatggc     300
cagggcttta gctatccgta taaagcggtg tttagcaccc agggcccgcc gctggcgagc     360
ctgcaggata gccatttcct gaccgatgcg gatatggtga tgagctttgt gaacctggtg     420
gaacatgata aagaattttt ttatccgcgc tatcatcatc gcgaatttcg ctttgatctg     480
agcaaaattc cggaaggcga agcggtgacc gcggcggaat ttcgcattta taaagattat     540
attcgcgaac gctttgataa cgaaaccttt cgcattagcg tgtatcaggt gctgcaggaa     600
catctgggcc gcgaaagcga tctgtttctg ctggatagcc gcaccctgtg ggcgagcgaa     660
gaaggctggc tggtgtttga tattaccgcg accagcaacc attgggtggt gaacccgcgc     720
```

```
cataacctgg gcctgcagct gtgcgtggaa accctggatg ccagagcat taacccgaaa      780 ctggcgggcc tgattggccg ccatggcccg cagaacaaac agccgtttat ggtggcgttt     840
tttaaagcga ccgaagtgca tctgcgcagc acccgcagca ccggcgcgaa acagcgcagc     900
cagaaccgca gcaaaacccc gaaaaaccag gaagcgctgc gcgtggcgaa cgtggcggaa     960
aacagcagca gcgatcagcg ccaggcgtgc aaaaaacatg aactgtatgt gagctttcgc    1020
gatctgggct ggcaggattg gattattgcg ccggaaggct atgcggcgta ttattgcgaa    1080
ggcgaatgcg cgtttccgct gaacagctat atgaacgcga ccaaccatgc gattgtgcag    1140
accctggtgc atttattaa cccggaaacc gtgccgaaac cgtgctgcgc gccgacccag     1200
ctgaacgcga ttagcgtgct gtattttgat gatagcagca acgtgattct gaaaaaatat    1260
cgcaacatgg tggtgcgcgc gtgcggctgc cattaa                              1296
```

<210> SEQ ID NO 3
<211> LENGTH: 431
<212> TYPE: PRT
<213> ORGANISM: Canis sp.

<400> SEQUENCE: 3

```
Met His Val Arg Ser Pro Cys Ala Ala Ala Pro Arg Ser Phe Val Ala
1               5                   10                  15

Leu Trp Ala Pro Leu Leu Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Asp Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe Tyr Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Cys Val Glu Thr Leu Asp Gly Gln Ser
                245                 250                 255

Ile Asn Pro Lys Leu Ala Gly Leu Ile Gly Arg His Gly Pro Gln Asn
            260                 265                 270
```

```
Lys Gln Pro Phe Met Val Ala Phe Phe Lys Ala Thr Glu Val His Leu
        275                 280                 285

Arg Ser Thr Arg Ser Thr Gly Ala Lys Gln Arg Ser Gln Asn Arg Ser
        290                 295                 300

Lys Thr Pro Lys Asn Gln Glu Ala Leu Arg Val Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
        340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
        420                 425                 430

<210> SEQ ID NO 4
<211> LENGTH: 69
<212> TYPE: DNA
<213> ORGANISM: Homo sapiens

<400> SEQUENCE: 4
atggatgcaa tgaagagagg gctctgctgt gtgctgctgc tgtgtggagc agtcttcgtt    60
tcgcccagc                                                            69

<210> SEQ ID NO 5
<211> LENGTH: 23
<212> TYPE: PRT
<213> ORGANISM: Homo sapiens

<400> SEQUENCE: 5

Met Asp Ala Met Lys Arg Gly Leu Cys Cys Val Leu Leu Leu Cys Gly
1               5                   10                  15

Ala Val Phe Val Ser Pro Ser
            20

<210> SEQ ID NO 6
<211> LENGTH: 84
<212> TYPE: DNA
<213> ORGANISM: Homo sapiens

<400> SEQUENCE: 6
atggatgcaa tgaagagagg gctctgctgt gtgctgctgc tgtgtggagc agtcttcgtt    60
tcgcccagcc aggaaatcca tgcc                                           84

<210> SEQ ID NO 7
<211> LENGTH: 28
<212> TYPE: PRT
<213> ORGANISM: Homo sapiens

<400> SEQUENCE: 7

Met Asp Ala Met Lys Arg Gly Leu Cys Cys Val Leu Leu Leu Cys Gly
1               5                   10                  15
```

Ala Val Phe Val Ser Pro Ser Gln Glu Ile His Ala
            20                  25

<210> SEQ ID NO 8
<211> LENGTH: 75
<212> TYPE: DNA
<213> ORGANISM: Equus sp.

<400> SEQUENCE: 8
atgcacatca tgagcagcag ccacctgttc tacctggccc tgtgcctgct gaccttcacc    60
agcagcgcca ccgcc                                                    75

<210> SEQ ID NO 9
<211> LENGTH: 25
<212> TYPE: PRT
<213> ORGANISM: Equus sp.

<400> SEQUENCE: 9

Met His Ile Met Ser Ser Ser His Leu Phe Tyr Leu Ala Leu Cys Leu
1               5                   10                  15

Leu Thr Phe Thr Ser Ser Ala Thr Ala
            20                  25

<210> SEQ ID NO 10
<211> LENGTH: 1296
<212> TYPE: DNA
<213> ORGANISM: Equus caballus

<400> SEQUENCE: 10
atgcacgtgc gctcgctgcg caccgcggcg ccccacagct tgtggcgcct ctgggcgccc    60
ctgttcctgc tgcgctccgc cctggccgac ttcagcctgg acaacgaggt gcactcgagc   120
ttcatccacc ggcgcctccg cagccaggag cggcgggaga tgcagcgcga gatcctctcc   180
atcttgggtt tgccccatcg cccgcgcccc cacctccagg gcaagcacaa ctcggcgccc   240
atgttcatgc tggacctgta caatgccatg gcggtggagg agagcggcgg gcccgacggc   300
cagggcttct cctaccccca aaggccgtc tccagtaccc agggccccc tctggccagc   360 ctgcaagata gccacttcct caccgacgcc gacatggtca tgagcttcgt caaccttgtg   420
gaacacgaca aagagttctt tcaccgcgc taccaccatc gggagttccg gtttgatctt   480
tccaagatcc cagaagggga ggccgtgact gcggccgagt tccggatcta caaggattac   540
gtccgggagc gcttcgataa cgagacgttc cgcatcagcg tgtaccaagt gctgcaggag   600
cacctggcca gggagtcgga cctgttcctg cttgacagcc gcaccctctg ggcctcagag   660
gagggctggc tggtgttcga catcacagcc accagcaacc actgggtggt caacccacgg   720
cacaatctgg gcctgcagct ctcggtggag accttggacg ggcagagcgt gaacccaag    780 ctggcgggcc tgatcgggcg gcacggcccc cagaccaagc agcctttcat ggtcgccttc   840
ttcaaggcca ccgaggtcca ccttcgcagc acccgctcca cgggcggcaa gcagcgcagc   900
cagaaccgct ccaagacgcc caagaaccag gaggccctgc gggtggccaa tgtcgcagag   960
aacagcagca gcgaccagag gcaggcctgt aagaagcacg agctgtacgt cagcttccgc  1020
gacctgggct ggcaggactg gatcatcgca cccgaaggct atgccgccta ctactgcgag  1080
ggagagtgcg ccttcccgct gaactcctac atgaacgcca ccaaccacgc catcgtgcag  1140
acactggtcc acttcatcaa cccagagacg gtgcccaagc cttgctgtgc acccacgcag  1200
ctgaacgcca tctccgtcct ctactttgac gacagctcca acgtcatcct gaagaaatac  1260

```
agaaacatgg tcgtccgggc ctgtggctgc cactag                      1296

<210> SEQ ID NO 11
<211> LENGTH: 75
<212> TYPE: DNA
<213> ORGANISM: Canis sp.

<400> SEQUENCE: 11
atgcacaccg tgtcctcctc gcacctcttc tacctggcac tgtgcttgct caccttcccc    60
agccccgcca cagct                                                    75

<210> SEQ ID NO 12
<211> LENGTH: 25
<212> TYPE: PRT
<213> ORGANISM: Canis sp.

<400> SEQUENCE: 12

Met His Thr Val Ser Ser Ser His Leu Phe Tyr Leu Ala Leu Cys Leu
1               5                   10                  15

Leu Thr Phe Pro Ser Pro Ala Thr Ala
            20                  25

<210> SEQ ID NO 13
<211> LENGTH: 1296
<212> TYPE: DNA
<213> ORGANISM: Homo sapiens

<400> SEQUENCE: 13
atgcacgtgc gctcactgcg agctgcggcg ccgcacagct tcgtggcgct ctgggcaccc    60
ctgttcctgc tgcgctccgc cctggccgac ttcagcctgg acaacgaggt gcactcgagc   120
ttcatccacc ggcgcctccg cagccaggag cggcgggaga tgcagcgcga tcctctcc    180 attttgggct tgccccaccg cccgcgcccc cacttccagg gcaagcacaa ctcggcaccc   240
atgttcatgc tggacctgta caacgccatg gcggtggagg agggcggcgg gccccggcggc   300 cagggcttct cctaccccta caaggccgtc ttcagtaccc agggccccc tctggccagc   360 ctgcaagata gccatttcct caccgacgcc gacatggtca tgagcttcgt caacctcgtg   420
gaacatgaca aggaattctt ccacccacgc taccaccatc gagagttccg gtttgatctt   480
tccaagatcc agaagggga agctgtcacg gcagccgaat tccggatcta caaggactac   540
atccgggaac gcttcgacaa tgagacgttc cggatcagcg tttatcaggt gctccaggag   600
cacttgggca gggaatcgga tctcttcctg ctcgacagcc gtaccctctg ggcctcggag   660
gagggctggc tggtgtttga catcacagcc accagcaacc actgggtggt caatccgcgg   720
cacaacctgg gcctgcagct ctcggtggag acgctggatg gcagagcat caaccccaag   780 ttggcgggcc tgattggcg gcacgggccc cagaacaagc agcccttcat ggtggctttc   840
ttcaaggcca cggaggtcca cttccgcagc atccggtcca cggggagcaa acagcgcagc   900
cagaaccgct ccaagacgcc caagaaccag gaagccctgc ggatggccaa cgtggcagag   960
aacagcagca gcgaccagag gcaggcctgt aagaagcacg agctgtatgt cagcttccga  1020
gacctgggct ggcaggactg gatcatcgcg cctgaaggct acgccgccta ctactgtgag  1080
ggggagtgtg ccttccctct gaactcctac atgaacgcca ccaaccacgc catcgtgcag  1140
acgctggtcc acttcatcaa cccggaaacg gtgcccaagc cctgctgtgc gcccacgcag  1200
ctcaatgcca tctccgtcct ctacttcgat gacagctcca acgtcatcct gaagaaatac  1260
```

```
agaaacatgg tggtccgggc ctgtggctgc cactag                          1296
```

<210> SEQ ID NO 14
<211> LENGTH: 1299
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14

```
atgcacgtgc ggagcctgag agccgctgcc ccccacagct tcgtggccct gtgggcccct   60
ctgttcctgc tgcggagcgc cctggccgac ttcagcctgg acaacgaggt gcacagcagc  120
ttcatccacc ggcggctgcg gagccaggaa cggcgggaga tgcagcggga gatcctgagc  180
atcctgggcc tgcctcaccg gcccaggcct cacctgcagg gcaagcacaa cagcgccccc  240
atgttcatgc tggacctgta caacgccatg gccgtggagg aaggcggcgg acctggcggc  300
cagggcttca gctaccccta caaggccgtg ttcagcacac agggccctcc tctggccagc  360
ctgcaggaca gccacttcct gaccgacgcc gacatggtga tgagcttcgt gaacctggtg  420
gagcacgaca aagagttctt ccaccccaga taccaccacc gggagttccg gttcgacctg  480
agcaagatcc ccgagggcga ggccgtgaca gccgccgagt ccggatctca aggactac    540
atccgggagc ggttcgacaa cgagaccttc cggatcagcg tgtaccaggt gctgcaggaa  600
cacctgggcc gggagagcga cctgtttctg ctggacagcc ggacactgtg gccagcgag   660
gaaggctggc tggtgttcga catcaccgcc acctccaacc actgggtggt gaaccccgg   720
cacaatctgg gcctgcagct gtccgtggag accctggacg ccagagcat caaccccaag   780
ctggccggcc tgatcggcag acacggcccc cagaacaagc agcccttcat ggtggccttt   840
ttcaaggcca ccgaggtgca cttcagaagc atccggtcca ccggcagcaa gcagcggagc   900
cagaacagaa gcaagacccc caagaaccag gaagccctgc ggatggccaa cgtggccgag   960
aacagcagca gcgaccagcg gcaggcctgc aagaagcacg agctgtacgt cagcttccgg  1020
gacctgggct ggcaggactg gatcatcgcc cccgagggct acgccgccta ctactgcgag  1080
ggcgagtgcg ccttcccccct gaacagctac atgaacgcca ccaaccacgc catcgtgcag  1140
accctggtgc actttatcaa ccccgagacc gtgcccaagc cctgctgcgc ccccacccag  1200
ctgaacgcca tcagcgtgct gtacttcgac gacagcagca acgtgatcct gaagaaatac  1260
cggaacatgg tggtgcgggc ctgcggctgc cactgataa                         1299
```

<210> SEQ ID NO 15
<211> LENGTH: 431
<212> TYPE: PRT
<213> ORGANISM: Homo sapiens

<400> SEQUENCE: 15

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80
```

```
Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 16
<211> LENGTH: 431
<212> TYPE: PRT
<213> ORGANISM: Equus caballus

<400> SEQUENCE: 16

Met His Val Arg Ser Leu Arg Thr Ala Ala Pro His Ser Phe Val Ala
1               5                   10                  15

Leu Trp Ala Pro Leu Phe Leu Leu Arg Ser Ala Leu Ala Asp Phe Ser
```

```
                    20                  25                  30
Leu Asp Asn Glu Val His Ser Ser Phe Ile His Arg Arg Leu Arg Ser
            35                  40                  45
Gln Glu Arg Arg Glu Met Gln Arg Glu Ile Leu Ser Ile Leu Gly Leu
        50                  55                  60
Pro His Arg Pro Arg Pro His Leu Gln Gly Lys His Asn Ser Ala Pro
65                  70                  75                  80
Met Phe Met Leu Asp Leu Tyr Asn Ala Met Ala Val Glu Glu Ser Gly
                85                  90                  95
Gly Pro Asp Gly Gln Gly Phe Ser Tyr Pro His Lys Ala Val Ser Ser
            100                 105                 110
Thr Gln Gly Pro Pro Leu Ala Ser Leu Gln Asp Ser His Phe Leu Thr
        115                 120                 125
Asp Ala Asp Met Val Met Ser Phe Val Asn Leu Val Glu His Asp Lys
130                 135                 140
Glu Phe Phe His Pro Arg Tyr His His Arg Glu Phe Arg Phe Asp Leu
145                 150                 155                 160
Ser Lys Ile Pro Glu Gly Glu Ala Val Thr Ala Ala Glu Phe Arg Ile
                165                 170                 175
Tyr Lys Asp Tyr Val Arg Glu Arg Phe Asp Asn Glu Thr Phe Arg Ile
            180                 185                 190
Ser Val Tyr Gln Val Leu Gln Glu His Leu Ala Arg Glu Ser Asp Leu
        195                 200                 205
Phe Leu Leu Asp Ser Arg Thr Leu Trp Ala Ser Glu Glu Gly Trp Leu
210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Val Asn Pro Lys Leu Ala Gly Leu Ile Gly Arg His Gly Pro Gln Thr
            260                 265                 270
Lys Gln Pro Phe Met Val Ala Phe Phe Lys Ala Thr Glu Val His Leu
        275                 280                 285
Arg Ser Thr Arg Ser Thr Gly Gly Lys Gln Arg Ser Gln Asn Arg Ser
290                 295                 300
Lys Thr Pro Lys Asn Gln Glu Ala Leu Arg Val Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
    370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 17
```

<211> LENGTH: 1296
<212> TYPE: DNA
<213> ORGANISM: Felis catus

<400> SEQUENCE: 17

| | |
|---|---|
| atgcacgtgc gctcgctgcg cgccgcggcg ccccacagct tcgtggcgct ctgggcgccc | 60 |
| ctgttcctgc tgcgctccgc cctggccgac ttcagcctgg acaacgaggt gcactcgagc | 120 |
| ttcatccacc ggcgcctccg cagccaggag cggcgggaga tgcagcgcga gatcctctct | 180 |
| atcttgggct tgccccatcg cccgcgcccc cacctccagg gcaagcacaa ctcggcgccc | 240 |
| atgttcatgc tggacctgta caacgccatg gcggtggagg agggcggcgg gcccgacggc | 300 |
| cagggcttct cctaccccta caaggccgtc ttcagtaccc agggcccccc tctggccagc | 360 |
| ctgcaagata gccgcttcct caccgacgcc gacatggtca tgagcttcgt caacctcgtg | 420 |
| gagcacgaca aagagttctt ccacccacgt taccaccacc gggagttccg gtttgatctt | 480 |
| tccaagatcc cagaagggga agccgtgacc gcagccgaat ccgcatctta aaggactac | 540 |
| atccgggaac gctttgataa tgagacgttc cggatcagcg tttaccaggt gcttcaggag | 600 |
| cacttgggca gggagtccga cctgttcctg ctggacagcc gcacgctctg ggcctcggag | 660 |
| gagggctggc tggtgttcga catcacggcc accagcaacc actgggtggt caacccgcgg | 720 |
| cacaatctgg gcctgcagct ctgcgtggag accttggacg ggcagagcat caaccccaag | 780 |
| ttggcgggcc tgatcgggag gcacgggccc cagaacaagc agcccttcat ggtggccttc | 840 |
| ttcaaggcca cggaggtcca ccttcgcagc acccgctcca caggggcaa gcaacgcagc | 900 |
| cagaaccgct ccaagacgcc caagaaccag gaagccctgc gggtgaccaa cgtcgcagaa | 960 |
| aacagcagca gtgaccagag gcaggcttgt aagaagcacg agctgtacgt cagcttccgc | 1020 |
| gacctgggct ggcaggactg gatcatcgct cccgaaggct atgctgctta ctactgcgag | 1080 |
| ggggagtgtg ccttccctct gaactcctac atgaacgcca ccaaccacgc catcgtgcag | 1140 |
| acgctggtcc acttcatcaa cccggagacg gtgcccaagc cgtgctgtgc ccccacgcag | 1200 |
| ctcaacgcca tctctgtgct ctacttcgac gacagctcca cgtcatcct gaagaaatac | 1260 |
| agaaacatgg tcgtccgagc ctgtggctgc cactag | 1296 |

<210> SEQ ID NO 18
<211> LENGTH: 1299
<212> TYPE: DNA
<213> ORGANISM: Artificial Sequence
<220> FEATURE:
<223> OTHER INFORMATION: Description of Artificial Sequence: Synthetic construct

<400> SEQUENCE: 18

| | |
|---|---|
| atgcacgtgc gctcactgcg agctgcggcg ccgcacagct tcgtggcgct ctgggcaccc | 60 |
| ctgttcctgc tgcgctccgc cctggccgac ttcagcctgg acaacgaggt gcactcgagc | 120 |
| ttcatccacc ggcgcctccg cagccaggag cggcgggaga tgcagcgcga gatcctctct | 180 |
| atcttgggct tgccccatcg cccgcgcccc cacctccagg gcaagcacaa ctcggcgccc | 240 |
| atgttcatgc tggacctgta caacgccatg gcggtggagg agggcggcgg gcccgacggc | 300 |
| cagggcttct cctaccccta caaggccgtc ttcagtaccc agggcccccc tctggccagc | 360 |
| ctgcaagata gccgcttcct caccgacgcc gacatggtca tgagcttcgt caacctcgtg | 420 |
| gagcacgaca aagagttctt ccacccacgt taccaccacc gggagttccg gtttgatctt | 480 |
| tccaagatcc cagaagggga agccgtgacc gcagccgaat ccgcatctta aaggactac | 540 |

```
atccgggaac gctttgataa tgagacgttc cggatcagcg tttaccaggt gcttcaggag    600
cacttgggca gggagtctga cctgttcctg ctggacagcc gtacgctctg ggcctcggag    660
gagggctggc tggtgttcga catcacggcc accagcaacc actgggtggt caacccgcgg    720
cacaatctgg gcctgcagct ctgcgtggag accttggacg gcagagcat caaccccaag     780 ttggcgggcc tgatcgggag cacgggccc cagaacaagc agcccttcat ggtggccttc     840
ttcaaggcca cggaggtcca ccttcgcagc acccgctcca caggggggcaa gcaacgcagc    900 cagaaccgct ccaagacgcc caagaaccag gaagccctgc gggtgaccaa cgtcgcagaa    960
aacagcagca gtgaccagag gcaggcttgt aagaagcacg agctgtacgt cagcttccgc    1020
gacctgggct ggcaggactg gatcatcgct cccgaaggct atgctgctta ctactgcgag    1080
ggggagtgtg ccttccctct gaactcctac atgaacgcca ccaaccacgc catcgtgcac    1140
acgctggtcc acttcatcaa cccggagacg gtgcccaagc cgtgctgtgc ccccacgcag    1200
ctcaacgcca tctctgtgct ctacttcgac gacagctcca acgtcatcct gaagaaatac    1260
agaaacatgg tcgtccgagc ctgtggctgc cactagtag                           1299
```

<210> SEQ ID NO 19
<211> LENGTH: 431
<212> TYPE: PRT
<213> ORGANISM: Felis catus

<400> SEQUENCE: 19

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Asp Gly Gln Gly Phe Ser Tyr Pro Tyr Lys Ala Val Phe Ser
            100                 105                 110

Thr Gln Gly Pro Pro Leu Ala Ser Leu Gln Asp Ser Arg Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240
```

His Asn Leu Gly Leu Gln Leu Cys Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Leu
        275                 280                 285

Arg Ser Thr Arg Ser Thr Gly Gly Lys Gln Arg Ser Gln Asn Arg Ser
290                 295                 300

Lys Thr Pro Lys Asn Gln Glu Ala Leu Arg Val Thr Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggatccctag tggcagccac aggctcggac g                              31

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gccaccagca accactgggt ggtc                                      24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ttcagcctgg acaacgaggt gcac                                      24

<210> SEQ ID NO 23
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 23
tggttggtgg cgttcatgta                                                20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gggtagcgcg tagagccggc gcg                                            23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgtcggtgag gaagcggctc ta                                             22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggatctcgcg ctgcatctcc cg                                             22

<210> SEQ ID NO 27
<211> LENGTH: 1293
<212> TYPE: DNA
<213> ORGANISM: Mus musculus

<400> SEQUENCE: 27
atgcacgtgc gctcgctgcg cgctgcggcg ccacacagct tcgtggcgct ctgggcgcct     60
ctgttcttgc tgcgctccgc cctggccgat tcagcctgg acaacgaggt gcactccagc    120
ttcatccacc ggcgcctccg cagccaggag cggcgggaga tgcagcggga gatcctgtcc    180
atcttagggt tgccccatcg cccgcgcccg cacctccagg gaaagcataa ttcggcgccc    240
atgttcatgt tggacctgta caacgccatg gcggtggagg agagcgggcc ggacggacag    300
ggcttctcct accctacaa ggccgtcttc agtacccagg ccccccttt agccagcctg      360 caggacagcc acttcctcac tgacgccgac atggtcatga gcttcgtcaa cctagtggaa    420
catgacaaag aattcttcca ccctcgatac caccatcggg agttccggtt tgatctttcc    480
aagatccccg agggcgaagc ggtgaccgca gccgaattca ggatctataa ggactacatc    540
cgggagcgat tgacaacga gaccttccag atcacagtct atcaggtgct ccaggagcac    600
tcaggcaggg agtcggacct cttcttgctg acagccgca ccatctgggc ttctgaggag    660
ggctggttgg tgtttgatat cacagccacc agcaaccact gggtggtcaa ccctcggcac    720
```

-continued

```
aacctgggct tacagctctc tgtggagacc ctggatgggc agagcatcaa ccccaagttg    780
gcaggcctga ttggacggca tggaccccag aacaagcaac ccttcatggt ggccttcttc    840
aaggccacgg aagtccatct ccgtagtatc cggtccacgg ggggcaagca gcgcagccag    900
aatcgctcca agacgccaaa gaaccaagag gccctgagga tggccagtgt ggcagaaaac    960
agcagcagtg accagaggca ggcctgcaag aaacatgagc tgtacgtcag cttccgagac   1020
cttggctggc aggactggat cattgcacct gaaggctatg ctgcctacta ctgtgaggga   1080
gagtgcgcct tccctctgaa ctcctacatg aacgccacca ccacgccat cgtccagaca   1140 ctggttcact tcatcaaccc agacacagta cccaagccct gctgtgcgcc cacccagctc   1200
aacgccatct ctgtcctcta cttcgacgac agctctaatg tcatcctgaa gaagtacaga   1260
aacatggtgg tccgggcctg tggctgccac tag                                 1293
```

<210> SEQ ID NO 28
<211> LENGTH: 430
<212> TYPE: PRT
<213> ORGANISM: Mus musculus

<400> SEQUENCE: 28

```
Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Ala Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270
```

```
Gln Pro Phe Met Val Ala Phe Phe Lys Ala Thr Glu Val His Leu Arg
        275                 280                 285

Ser Ile Arg Ser Thr Gly Gly Lys Gln Arg Ser Gln Asn Arg Ser Lys
        290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
                340                 345                 350

Tyr Ala Ala Tyr Tyr Cys Glu Gly Glu Cys Ala Phe Pro Leu Asn Ser
        355                 360                 365

Tyr Met Asn Ala Thr Asn His Ala Ile Val Gln Thr Leu Val His Phe
        370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
                405                 410                 415

Lys Lys Tyr Arg Asn Met Val Val Arg Ala Cys Gly Cys His
                420                 425                 430

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcagtcatag ccatcgacag a                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtgctggctg gcacgggcat t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atgtccacca aagtcccctc t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 32
cccggggcgt cgtatggata t                                              21

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gatacgcgtt ccattagcag atct                                           24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggacaccttt ctgatcagtt catt                                           24

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatacgcgtt ccattagcag atctttgagg ggcctggaaa taggc                    45

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggttgtgtgg aagacccggg ggcg                                           24

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
agatctgcta atggaacgcg tatcgctgcc cccacagtac agcaa                    45

<210> SEQ ID NO 38
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
```

-continued ctagtcatct taacgcgtgt cctcaacatc acccgcga                          38

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cttgcttgtt attaaaaaaa g                                           21

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
atcttaacgc gtccctcagc cttctaatgg gac                              33

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atcgtaaagc ttaatgtcgt aataccccg c                                 31

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tctactgcag ccggtgtctt ctatggaggt ca                               32

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcttcgcccc cgttttcacc atgg                                        24

<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

-continued atcacgccgc ggcttaaaaa aattacgccc cgcc      34

<210> SEQ ID NO 45
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
aattcggtac caagcttctt tattctatac ttaaaaagtg aaaataaata caaaggttct      60
tgactctctt c      71

<210> SEQ ID NO 46
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cgcatcgctg tctgcgaggg ccagctgttg ggctcgcggt tgaggacaaa ctcttcgcgg      60
tctttccagt      70

<210> SEQ ID NO 47
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
actcttggat cggaaacccg tcggcctccg aacgtactcc gccaccgagg gacctgagcg      60
agtccgcatc      70

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gaccggatcg gaaacctct cgagaaaggc gtctaaccag tcacagtcgc aagcccgggt      60

<210> SEQ ID NO 49
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ctttgtattt attttcactt tttaagtata gaataaagaa gcttggtacc g      51

<210> SEQ ID NO 50
<211> LENGTH: 72
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 50
gaagagtttg tcctcaaccg cgagcccaac agctggccct cgcagacagc gatgcggaag    60
agagtcaaga ac                                                        72

<210> SEQ ID NO 51
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gctcaggtcc ctcggtggcg gagtacgttc ggaggccgac gggtttccga tccaagagta    60
ctggaaagac cgc                                                       73

<210> SEQ ID NO 52
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ctagacccgg gcttgcgact gtgactggtt agacgccttt ctcgagaggt tttccgatcc    60
ggtcgatgcg gactc                                                     75

<210> SEQ ID NO 53
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atcgtcctgc agactctctt ccgcatcgct gtctgc                              36

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gctctagact tgcgactgtg actggttag                                      29

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
cgtttagtga accgtctgca                                                20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gacggttcac taaacgagct                                                   20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gtaaaaacga cggccagt                                                     18

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
atcgtcccgc ggaattgttg ttgttaactt gtt                                    33

<210> SEQ ID NO 59
<211> LENGTH: 537
<212> TYPE: DNA
<213> ORGANISM: Equus caballus

<400> SEQUENCE: 59
atgcacagct cagcactgct atgttacctg gtcttcctgg ccggggtggg agccagccga        60
gaccggggca cccagtctga aacagctgc acccacttcc caaccagcct gccccacatg       120
ctccatgagc tccgagccgc cttcagcagg gtgaagactt tctttcaaat gaaggaccag      180
ctggacaaca tgttgttgaa cgggtccctg ctggaggact taagggtta cctgggttgc       240 caagccttgt cggagatgat ccagttttac ctggaggagg tgatgcccca ggctgagaac      300
cacggcccag acatcaagga gcacgtgaac tccctggggg aaaagctgaa gaccctccga      360
gtgaggctgc ggcgctgtca tcgatttctg ccctgtgaaa ataagagcaa ggcagtggag      420
caggtgaaga gtgccttcag taagctccaa gagaaaggtg tctacaaagc catgagtgag      480
tttgacatct tcatcaacta catagaagcc tatatgacaa cgaagatgaa aaactga         537

<210> SEQ ID NO 60
<211> LENGTH: 178
<212> TYPE: PRT
<213> ORGANISM: Equus caballus

<400> SEQUENCE: 60

Met His Ser Ser Ala Leu Leu Cys Tyr Leu Val Phe Leu Ala Gly Val
1               5                   10                  15

Gly Ala Ser Arg Asp Arg Gly Thr Gln Ser Glu Asn Ser Cys Thr His
            20                  25                  30

Phe Pro Thr Ser Leu Pro His Met Leu His Glu Leu Arg Ala Ala Phe

```
                35                    40                    45
Ser Arg Val Lys Thr Phe Phe Gln Met Lys Asp Gln Leu Asp Asn Met
    50                  55                  60

Leu Leu Asn Gly Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn His Gly Pro Asp Ile Lys Glu His Val Asn Ser Leu
                100                 105                 110

Gly Glu Lys Leu Lys Thr Leu Arg Val Arg Leu Arg Arg Cys His Arg
            115                 120                 125

Phe Leu Pro Cys Glu Asn Lys Ser Lys Ala Val Glu Gln Val Lys Ser
        130                 135                 140

Ala Phe Ser Lys Leu Gln Glu Lys Gly Val Tyr Lys Ala Met Ser Glu
145                 150                 155                 160

Phe Asp Ile Phe Ile Asn Tyr Ile Glu Ala Tyr Met Thr Thr Lys Met
                165                 170                 175

Lys Asn

<210> SEQ ID NO 61
<211> LENGTH: 540
<212> TYPE: DNA
<213> ORGANISM: Canis lupus

<400> SEQUENCE: 61
atgcccagcc cagcactgct ctgttgctgc ctggtcctcc tggccggggt gggagccagc      60
cgacaccaga gcaccctacc tgaggacgac tgcacccact cccagccag cctgccccac      120 atgctccgag agctccgagc tgccttcggg agggtgaaga ctttctttca atgaaggac      180 aagctggaca catactgct gaccgggtcc ctgctggagg actttaagag ttacctgggt      240
tgccaagccc tgtcggagat gatccagttt tacttggagg aggtgatgcc ccgggctgag      300
aaccacgacc agacatcaa gaaccacgtg aactccctgg gagagaagct caagaccctc      360
aggctgaggc tgcgacgctg tcaccgattt ctgccctgtg agaataagag caaggcggtg      420
gagcaggtga agagcgcatt tagtaagctc caggagaaag gtgtctacaa agccatgagt      480
gagtttgaca tcttcatcaa ctacatagaa acctacatga caatgaggat gaaaatctga      540

<210> SEQ ID NO 62
<211> LENGTH: 179
<212> TYPE: PRT
<213> ORGANISM: Canis lupus

<400> SEQUENCE: 62

Met Pro Ser Pro Ala Leu Leu Cys Cys Cys Leu Val Leu Leu Ala Gly
1               5                   10                  15

Val Gly Ala Ser Arg His Gln Ser Thr Leu Pro Glu Asp Asp Cys Thr
                20                  25                  30

His Phe Pro Ala Ser Leu Pro His Met Leu Arg Glu Leu Arg Ala Ala
            35                  40                  45

Phe Gly Arg Val Lys Thr Phe Phe Gln Met Lys Asp Lys Leu Asp Asn
        50                  55                  60

Ile Leu Leu Thr Gly Ser Leu Leu Glu Asp Phe Lys Ser Tyr Leu Gly
65                  70                  75                  80

Cys Gln Ala Leu Ser Glu Met Ile Gln Phe Tyr Leu Glu Glu Val Met
                85                  90                  95
```

```
Pro Arg Ala Glu Asn His Asp Pro Asp Ile Lys Asn His Val Asn Ser
            100                 105                 110

Leu Gly Glu Lys Leu Lys Thr Leu Arg Leu Arg Leu Arg Arg Cys His
        115                 120                 125

Arg Phe Leu Pro Cys Glu Asn Lys Ser Lys Ala Val Glu Gln Val Lys
    130                 135                 140

Ser Ala Phe Ser Lys Leu Gln Glu Lys Gly Val Tyr Lys Ala Met Ser
145                 150                 155                 160

Glu Phe Asp Ile Phe Ile Asn Tyr Ile Glu Thr Tyr Met Thr Met Arg
                165                 170                 175

Met Lys Ile

<210> SEQ ID NO 63
<211> LENGTH: 537
<212> TYPE: DNA
<213> ORGANISM: Felis catus

<400> SEQUENCE: 63
atgcacagct cagcacttct gtgtttcctg gtcttcctgg ccggggtagg agccagccga      60
caccagagca ccctgtctga ggacaactgc acccacttct cagtcagcct gccccacatg     120
ctccragagc tccgagctgc cttcggcaag gtgaagactt tctttcaaac caaggacgag     180
ctgcacagca tattgttgac caggtccttg ctggaggact ttaagggtta cctgggttgc     240
caagccttgt ccgagatgat ccagttttat ttggaggagg tgatgcccca ggctgagaac     300
gaggacccag acatcaaaca gcacgtgaac tccctgggag aaaagctgaa gaccctccgg     360
ctgagactgc ggcgctgtca tcgatttctg ccctgtgaaa acaagagcaa ggtggtggag     420
caggtgaaga gtacctttag taagctccaa gagaaaggtg tctacaaagc catgggtgag     480
tttgacatct tcatcaacta catagaagct tacatgacaa tgaagatgaa aatctga        537

<210> SEQ ID NO 64
<211> LENGTH: 178
<212> TYPE: PRT
<213> ORGANISM: Felis catus
<220> FEATURE:
<221> NAME/KEY: MOD_RES
<222> LOCATION: (42)..(42)
<223> OTHER INFORMATION: Variable amino acid

<400> SEQUENCE: 64

Met His Ser Ser Ala Leu Leu Cys Phe Leu Val Phe Leu Ala Gly Val
1               5                   10                  15

Gly Ala Ser Arg His Gln Ser Thr Leu Ser Glu Asp Asn Cys Thr His
            20                  25                  30

Phe Ser Val Ser Leu Pro His Met Leu Xaa Glu Leu Arg Ala Ala Phe
        35                  40                  45

Gly Lys Val Lys Thr Phe Phe Gln Thr Lys Asp Glu Leu His Ser Ile
    50                  55                  60

Leu Leu Thr Arg Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Glu Asp Pro Asp Ile Lys Gln His Val Asn Ser Leu
            100                 105                 110

Gly Glu Lys Leu Lys Thr Leu Arg Leu Arg Leu Arg Arg Cys His Arg
        115                 120                 125
```

Phe Leu Pro Cys Glu Asn Lys Ser Lys Val Glu Gln Val Lys Ser
        130                 135                 140

Thr Phe Ser Lys Leu Gln Glu Lys Gly Val Tyr Lys Ala Met Gly Glu
145                 150                 155                 160

Phe Asp Ile Phe Ile Asn Tyr Ile Glu Ala Tyr Met Thr Met Lys Met
                165                 170                 175

Lys Ile

<210> SEQ ID NO 65
<211> LENGTH: 537
<212> TYPE: DNA
<213> ORGANISM: Homo sapiens

<400> SEQUENCE: 65
atgcacagct cagcactgct ctgttgcctg gtcctcctga ctggggtgag ggccagccca    60
ggccagggca cccagtctga aacagctgc acccacttcc caggcaacct gcctaacatg   120
cttcgagatc tccgagatgc cttcagcaga gtgaagactt tctttcaaat gaaggatcag   180
ctggacaact tgttgttaaa ggagtccttg ctggaggact taagggtta cctgggttgc   240 caagccttgt ctgagatgat ccagttttac ctggaggagg tgatgcccca agctgagaac   300
caagacccag acatcaaggc gcatgtgaac tccctggggg agaacctgaa gaccctcagg   360
ctgaggctac ggcgctgtca tcgatttctt ccctgtgaaa acaagagcaa ggccgtggag   420
caggtgaaga atgcctttaa taagctccaa gagaaaggca tctacaaagc catgagtgag   480
tttgacatct tcatcaacta catagaagcc tacatgacaa tgaagatacg aaactga     537

<210> SEQ ID NO 66
<211> LENGTH: 178
<212> TYPE: PRT
<213> ORGANISM: Homo sapiens

<400> SEQUENCE: 66

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 67
<211> LENGTH: 528
<212> TYPE: DNA
<213> ORGANISM: Human herpesvirus 5

<400> SEQUENCE: 67

```
atgctgtcgg tgatggtctc ttcctctctg gtcctgatcg tcttttttct aggcgcttcc      60
gaggaggcga agccggcgac gacgacgata aagaatacaa agccgcagtg tcgtccagag     120
gattacgcga ccagattgca agatctccgc gtcacctttc atcgagtaaa acctacgttg     180
caacgtgagg acgactactc cgtgtggctc gacggtacgg tggtcaaagg ctgttgggga     240
tgcagcgtca tggactggtt gttgaggcgg tatctggaga tcgtgtttcc cgcaggcgac     300
cacgtctatc ccggactcaa gacggaattg catagtatgc gctcgacgct agaatccatc     360
tacaaagaca tgcggcaatg tcctctgtta ggttgcggag ataagtccgt gattagtcgg     420
ctgtctcagg aggcggaaag gaaatcggat aacggcacgc ggaaaggtct cagcgagttg     480
gacacgttgt ttagccgtct cgaagagtat ctgcactcga gaaagtag                  528
```

<210> SEQ ID NO 68
<211> LENGTH: 175
<212> TYPE: PRT
<213> ORGANISM: Human herpesvirus 5

<400> SEQUENCE: 68

```
Met Leu Ser Val Met Val Ser Ser Ser Leu Val Leu Ile Val Phe Phe
1               5                  10                  15

Leu Gly Ala Ser Glu Glu Ala Lys Pro Ala Thr Thr Thr Ile Lys Asn
            20                  25                  30

Thr Lys Pro Gln Cys Arg Pro Glu Asp Tyr Ala Thr Arg Leu Gln Asp
        35                  40                  45

Leu Arg Val Thr Phe His Arg Val Lys Pro Thr Leu Gln Arg Glu Asp
    50                  55                  60

Asp Tyr Ser Val Trp Leu Asp Gly Thr Val Val Lys Gly Cys Trp Gly
65                  70                  75                  80

Cys Ser Val Met Asp Trp Leu Leu Arg Arg Tyr Leu Glu Ile Val Phe
                85                  90                  95

Pro Ala Gly Asp His Val Tyr Pro Gly Leu Lys Thr Glu Leu His Ser
            100                 105                 110

Met Arg Ser Thr Leu Glu Ser Ile Tyr Lys Asp Met Arg Gln Cys Pro
        115                 120                 125

Leu Leu Gly Cys Gly Asp Lys Ser Val Ile Ser Arg Leu Ser Gln Glu
    130                 135                 140

Ala Glu Arg Lys Ser Asp Asn Gly Thr Arg Lys Gly Leu Ser Glu Leu
145                 150                 155                 160

Asp Thr Leu Phe Ser Arg Leu Glu Glu Tyr Leu His Ser Arg Lys
                165                 170                 175
```

<210> SEQ ID NO 69
<211> LENGTH: 4
<212> TYPE: PRT
<213> ORGANISM: artificial
<220> FEATURE:

```
-continued
<223> OTHER INFORMATION: protein motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 69

Arg Xaa Xaa Arg
1
```